United States Patent [19]

Hou et al.

[11] Patent Number: 4,639,513

[45] Date of Patent: Jan. 27, 1987

[54] INTRAVENOUSLY INJECTABLE IMMUNOGLOBULIN G (IGG) AND METHOD FOR PRODUCING SAME

[75] Inventors: Kenneth C. Hou, Glastonbury; Garrett Cogswell, Vernon, both of Conn.

[73] Assignee: Cuno Inc., Meriden, Conn.

[21] Appl. No.: 656,922

[22] Filed: Oct. 2, 1984

Related U.S. Application Data

[63] Continuation-in-part of Ser. No. 576,448, Feb. 2, 1984, which is a continuation-in-part of Ser. No. 466,114, Feb. 14, 1983, abandoned, and a continuation-in-part of Ser. No. 643,212, Aug. 22, 1984 abandoned, and a continuation-in-part of Ser. No. 643,613, Aug. 22, 1984.

[51] Int. Cl.$^4$ .................. A61K 37/04; C07K 3/20
[52] U.S. Cl. .................. 530/387; 530/362; 530/395; 530/412; 530/414; 530/416; 530/417; 530/830; 424/85; 424/101
[58] Field of Search .............. 260/112 B, 112 R, 121; 424/85, 101; 210/927; 530/387, 362, 395, 412, 530/414, 416, 419, 830

[56] References Cited

U.S. PATENT DOCUMENTS

| | | | |
|---|---|---|---|
| 3,449,316 | 6/1969 | Querry | 530/387 |
| 3,555,001 | 1/1971 | Wallis et al. | 530/387 |
| 3,607,857 | 9/1971 | Nelson | 530/387 |
| 3,664,994 | 5/1972 | Perper | 530/387 |
| 3,686,395 | 8/1972 | Stephan | 424/101 |
| 3,763,135 | 10/1973 | Shanbrom et al. | 530/387 |
| 3,869,436 | 3/1975 | Albinsson | 530/387 |
| 3,869,857 | 9/1971 | Nelson | 530/387 |
| 3,903,262 | 9/1975 | Pappenhagen et al. | 424/85 |
| 3,928,580 | 12/1978 | Fontaine | 530/387 |
| 3,998,946 | 12/1976 | Condie | 424/101 |
| 4,007,114 | 2/1977 | Ostreicher | 210/503 |
| 4,029,583 | 6/1977 | Chang et al. | 210/198 |
| 4,070,348 | 1/1978 | Kraemer et al. | 526/261 |
| 4,093,606 | 6/1978 | Coval | 530/387 |
| 4,136,094 | 1/1979 | Condie | 260/112 B |
| 4,164,495 | 8/1979 | Hansen | 530/387 |
| 4,165,370 | 8/1979 | Coval | 530/387 |
| 4,256,631 | 3/1981 | Yokoo et al. | 260/112 B |
| 4,272,521 | 6/1981 | Zuffi | 260/112 B |
| 4,276,283 | 6/1981 | Eibl et al. | 530/387 |
| 4,305,870 | 12/1981 | Liu et al. | 424/101 |
| 4,312,949 | 1/1982 | Ahrens | 424/85 |
| 4,384,954 | 5/1983 | Nakashima et al. | 210/263 |
| 4,384,957 | 5/1983 | Crowder, III et al. | 210/198.2 |
| 4,404,285 | 9/1983 | Hou | 530/387 |
| 4,464,165 | 8/1984 | Pallard | 210/927 |
| 4,496,461 | 1/1985 | Leeke | 210/198.2 |

OTHER PUBLICATIONS

Cohn, E. J. et al., J. Am. Chem. Soc., 68: 459 (1946).
Sgouris, J. T., Vox Sang, 13: 71–84 (1967).
Schultze, H. E. et al., Med. Wochenschr., 87: 1643–1650 (1962).
Nisonoff, A. et al., Science, 132: 1770–1771 (1960).
Barandun, S. et al., Vox Sang, 7: 157–174 (1962).
Fleishman, J. B. et al., Arch. Biochem. Biophys. Supp., 1: 174–180 (1962).
Edelman, G. N. et al., J. Am. Chem. Soc., 81: 3155 (1959).
Gunewardena, P. et al., Biochem. J., 99: 8 (1966).
Curling, J. M. et al., Vox Sang, 33: 97 (1977).
Soumela, H. et al., Vox Sang, 33: 37 (1977).
Baumstark et al., Arch. Biochem. Biophys., 108: 514 (1964).
Heystek et al., Vox Sang, 25: 113 (1973).
Cooper, T. G., The Tools of Biochemistry, John Wiley & Sons, New York (1977), pp. 378–390.

Primary Examiner—John Kight
Assistant Examiner—Garnette D. Draper

[57] ABSTRACT

A method for producing intravenously injectable IgG comprising a particulate separation step, an ion exchange separation step and an affinity separation step, and the substantially pure, intravenously injectable IgG produced by the method.

35 Claims, 13 Drawing Figures

| AREA% RT | AREA | TYPE | AR/HT | AREA% |
|---|---|---|---|---|
| 3.23 | 3389 | PB | 0.110 | 9.0002E-04 |
| 5.17 | 5958200 | BY | 0.299 | 1.582 |
| 6.36 | 5.3428E+07 | YY | 0.846 | 14.189 |
| 7.65 | 3.1251E+08 | YR | 0.957 | 82.993 |
| 12.32 | 3371200 | PB | 0.289 | 0.895 |
| 14.23 | 1276500 | BP | 0.461 | 0.339 |

TOTAL AREA = 3.765E+08
MUL FACTOR = 1.0000E+00

| AREA% RT | AREA | TYPE | AR/HT | AREA% |
|---|---|---|---|---|
| 1.91 | 7959 | BP | 0.117 | 0.003 |
| 5.0 | 122600 | PY | 0.204 | 0.049 |
| 7.55 | 2.4893E+08 | YB | 0.909 | 99.654 |
| 12.22 | 713300 | PY | 0.323 | 0.286 |
| 13.93 | 20392 | BY | 0.151 | 0.008 |

TOTAL AREA = 2.4979E+08
MUL FACTOR = 1.0000E+00

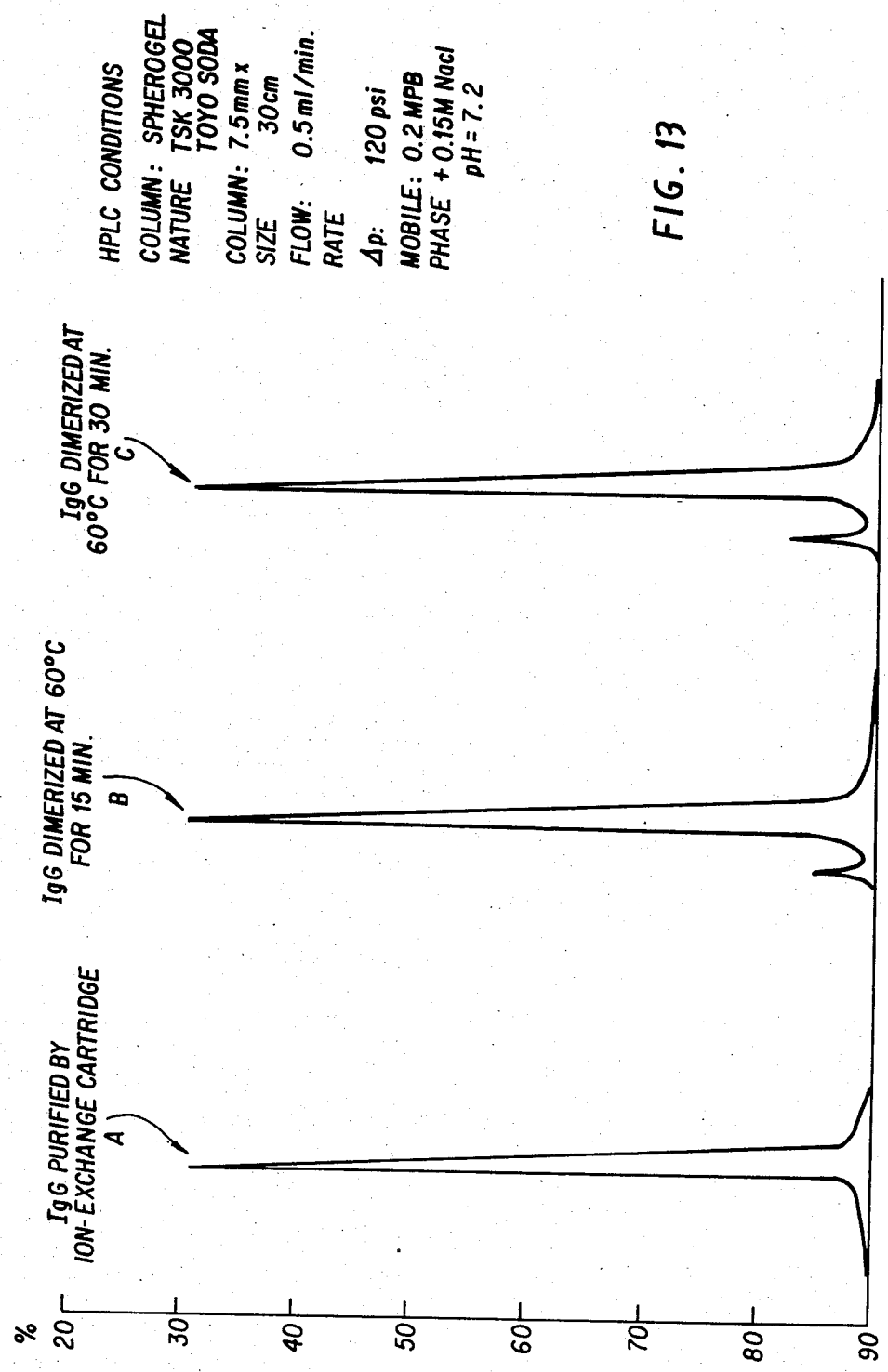

ND METHOD FOR
INTRAVENOUSLY INJECTABLE IMMUNOGLOBULIN G (IGG) AND METHOD FOR PRODUCING SAME

BACKGROUND OF THE INVENTION

This is a continuation-in-part of commonly assigned copending applications Ser. No. 576,448 filed Feb. 2, 1984, which is a continuation-in-part of application Ser. No. 466,114, filed Feb. 14, 1983, now abandoned; and a continuation-in-part of application Ser. No. 643,212, filed Aug. 22, 1984, now abandoned; and application Ser. No. 643,613, filed Aug. 23, 1984.

1. Field of the Invention

The present invention is directed to high purity immunoglobulin G (IgG) suitable for intravenous injection and to a method for producing the high purity IgG from animal plasma at high yields. The highly purified IgG of the present invention is remarkably free of aggregates, fragments, proteolytic enzymes, enzyme activators, coagulating factors, and the like, and has a much reduced anti-complementary activity. Additionally, useful high purity by-products such as prothrombin complex, transferin and albumin may be recovered.

2. Brief Description of the Background Art

Blood may be classified as a type of connective tissue with a liquid matrix. The extracellular liquid matrix of blood is called plasma, with formed elements suspended in the plasma. The three major types of formed elements in vertebrates are the red blood cells or erythrocytes, the white blood cells or leukocytes, and the platelets. The latter are small disc-shaped bodies that probably arise as cell fragments. Normally, the formed elements constitute about 40–50% of the volume of whole blood while the plasma constitutes the other 50–60%.

Plasma comprises approximately 90% water, the remaining approximately 10% comprising a variety of substances dissolved in the water as solutes. The solutes may be divided into six basic categories which are: (1) inorganic ions, (2) plasma proteins, (3) organic nutrients, (4) nitrogenous waste products, (5) special products being transported, and (6) dissolved gases. The plasma proteins constitute approximately 7–9% by weight of the plasma and are basically a mixture of lipoproteins, fibrinogens, albumins, and globulins.

Globulins are a class of proteins. Among the globulins are gamma globulins, a group of plasma globulins which have sites of antibody activity. These gamma globulins are also known as immunoglobulins, of which immunoglobulin G (IgG) is a major constituent.

The IgG fraction of pooled plasma contains antibodies to many viruses and bacteria and thus is effective in the clinical management of a wide variety of disease states. Representative uses of IgG include prophylaxis and therapy of infections in persons with genetic and nosocomial antibody deficiency states, especially staphylococci, pneumococci, streptococci, and *H. influenzae;* prophylaxis in patients with normal immunoglobulin levels of viral infections such as hepatitis, polio, measles, rubeola, rabies, herpes, and parotitis; prophylaxis in patients with normal immunoglobulin levels of tetanus and Rh-incompatability; and therapy of severe bacterial infections such as staphylococci, coli, pseudomonas, pyocyaneaus septicemias, and viral infections such as *Herpes zoster.*

While human immunoglobulins were first isolated on a large scale during World War II, intravenous injection of the conventional immunoglobulins is frequently accompanied by untoward side effects in the recipient, these side effects including anaphylaxis and the problems associated therewith. Included among the undesirable side effects caused by the intravenous injection of the prior art immunoglobulins are erythema, vomiting, abdominal pain, fever, and loss of consciousness. Accordingly, the use of IgG preparations for prophylactic and therapeutic purposes has been limited to administration primarily through intramuscular or subcutaneous injections. However, there are substantial limiting factors involved with the utilization of IgG through these routes such as maximum volume of solution which can be injected in each site, delay from the time of injection to the attainment of maximum antibody levels in the blood stream, loss of antibody during the passage from the injection site to the blood compartment, and severe discomfort at the site of administration.

The anaphylactoid reaction accompanying intravenous injection of gamma globulins has been associated with the decrease in serum complement levels, apparently caused by complement binding by the administered gamma globulin (S. Barandun, et al., *Vox Sang* 7:157–174 (1962)). It would appear that the ability of gamma globulin to bind complement, termed anticomplementary, is greatly increased as a result of a denaturation brought about during the previously known fractionation, i.e. Cohn fractionation, procedure by which the gamma globulin is purified. The complement binding mechanism of these aggregates appears to be identical to that of antigen-antibody complexes (D. M. Marcus, *J. Immunol.* 84:273–284 (1960)).

Intravenous administration of immunoglobulins has wider clinical application than intramuscular administration because the full dose of IgG enters the blood stream immediately without being degraded at the site of injection, and significantly higher IgG levels in the blood can be attained. Intravenous administration of IgG produces a high level of antibodies in patients with deficiencies in the humoral immune factor almost immediately, whereas it frequently requires one to several weeks for specific antibodies to be synthesized by the individual's immune mechanism and more than three days for a patient's blood level to reach 40% of the injected globulin dose where the injection is via the intramuscular route. The antibodies possess the ability to combine specifically with antigens such as viruses and bacteria, the resultant antigen and antibody complex either binding to macrophages or to complement factors by way of the Fc moiety of the antibody molecule, thereby initiating phagocytosis.

Human immunoglobulins are divided into five principal classes on the basis of chemical and isotypic properties. The five classes are IgG, IgA, IgM, IgD and IgE. Each of the classes of Ig molecules are made up of small (light) and large (heavy) polypeptide chains. Each of the five classes has similar sets of light chains, but an antigenically distinctive set of heavy chains. IgG immunoglobulins have a molecular weight of approximately 160,000 and constitute over 85% of the Ig's in the sera of most normal and hyperimmune individuals. The IgG proteins have 20–25 disulfide bonds per molecule with the molecule consisting of two heavy chains having a molecular weight each of about 50,000 and two light chains having a molecular weight each of about 25,000. Additionally, the proteins of the IgG class may be differentiated into four subclasses, IgG-1 through IgG-4, each with a distinct heavy chain. By the use of the term "IgG" herein is meant an immunoglobulin containing predominantly IgG, typically with all subclasses (1–4) and, optionally, minor amounts of the other immunoglobulins.

Prior to this invention immunoglobulins were mainly isolated from donor plasma or placentas by the Cohn fractionation method based on the differences in solubilities of plasma proteins in a multi-variable system by carefully controlling ethanol concentration, pH, ionic strength, temperature and protein concentration, Cohn, E. J., et al., *J. Am. Chem. Soc.* 68:459 (1946). However, because of the anti-complementary activity due to IgG aggregates formed during the fractionation process, it is necessary to further process the immunoglobulin obtained by Cohn fractionation in an effort to attain intravenous tolerance. Four basic procedures exist for further processing of immunoglobulin obtained by Cohn fractionation to prevent IgG aggregation, the four main procedures being:

1. enzymatic degradation by plasmin or pepsin;
2. chemical modification of the IgG molecule by beta-propiolactone or by cleavage of the interchain disulfide bridges by sulfonation or reduction and alkylation;
3. selective elimination of aggregates by precipitation with polyethylene glycol (PEG) and hydroxyethyl starch (HES) or by treatment at pH with traces of pepsin; and
4. adsorption of aggregates by DEAE gels such as Sephadex ® C50.

None of the procedures are completely satisfactory in producing highly pure IgG for intravenous use in a process which is commercially economical.

Enzymatic degradation by plasmin or pepsin is reported by Sgouris, J. T., *Vox Sang* 13:71–84 (1967) and Schultze, H. E., et al., *Ueber Neue Mog-Deutche Med. Wochenschr.* 87:1643–1650 (1962). Treatment of gamma globulin with pepsin at pH 4.0 results in proteolytic cleavage of the molecule to give a fragment of about 100,000 molecule weight, A. Nisonoff, et al., *Science* 132:1770:–1771 (1960). The surviving fragment retains bivalent antibody activity and lacks anticomplement activity and is well tolerated and efficacious in intravenous administration as reported by W. Baumgarten, *Vox Sang* 13:84 (1967). However, the therapeutic effect provided is of unacceptably short duration since the material is rapidly excreted, having a circulating half-life of only 18 hours, compared to 19.8 days for unmodified gamma globulin, E. Merler, et al., *Vox Sang* 13:102 (1967); B. Jager, *Arch. Intern. Intern. Med.* 119:60 (1967). An additional disadvantage of the pepsin treatment procedure is that the pepsin which remains present is of animal origin and can stimulate antibody production, particularly upon repeated administration, C. Blatrix, et al., *Presse Med.* 77:635–637 (1969).

Treatment of gamma globulin with human plasmin results in cleavage into three components of about 50,000 molecular weight, J. T. Sgouris, supra. When sufficiently low levels of plasmin are used, only about 15% of the molecules are cleaved, with 85% remaining as intact gamma globulin. The remaining intact gamma globulin shows little anti-complement activity and has been administered intravenously without adverse reactions, J. Hinman, et al., *Vox Sang* 13:85 (1967). The material has also been reported to retain in vitro and in vivo protective activity, S. K. Fitzpatrick, *Vox Sang*, 13:85 (1967). The disadvantages of such treatment of gamma globulin is that the plasmin must be removed from the IgG prior to administration Further, some of the IgG subclasses are found to be missing. Romer, et al., *Vox Sang* 42:62–73 (1982).

S. Barandun, et al., *Vox Sang* 7:157–174 (1962), reported on the effects of reduction of disulfide linkages of gamma globulin on anti-complementary activity. Treatment of a 7% solution of gamma globulin with 0.2M cysteamine, followed by 0.2M iodoacetamid resulted in almost complete loss of anti-complement activity. However, the toxicity of iodoacetamid makes this unsuitable for intravenously injectable gamma globulin. Mercaptoethanol, J. B. Fleishman, et al., *Arch. Biochem. & Biophys. Supp.* 1:174–180 (1972) and mercaptoethylamine, G. N. Edelman, *J. Am. Chem. Soc.* 81:3155 (1959), have been shown to be capable of reducing interchain disulfide bonds of gamma globulin. Disulfide bonds which are more labile to mercaptan reduction appear to be related to complement fixation, while the disulfide bonds which are more resistant to reduction by mercaptan appear to be related to interaction with antigens, C. H. Schur, et al., *J. Exp. Med.* 120:531 (1963). Virtually complete reduction of all the disulfide bonds of human gamma globulin has been achieved by the action of 0.0125M dithiothreitol (DTT) and a 2% gamma globulin solution, P. Gunewardena, et al., *Biochem. Journ.* 99:8 (1966); however, complete reduction would likely destroy all antibody activity. Again, these methods require subsequent removal of the compounds from the treated IgG.

U.S. Pat. No. 3,903,262 to Pappenhagen, et al., includes a rather comprehensive discussion of prior methods of purifying IgG and further reports on a claimed invention wherein an intravenously injectable substantially pure modified immune serum globulin consisting essentially of intact immune serum globulin chains having intact intrachain disulfide linkages and cleaved at at least one interchain disulfide linkage, each cleaved disulfide linkage being replaced by a pair of alkylated mercapto groups. The modified immune serum globulin is produced by selectively reducing a mildly alkaline aqueous solution with dithiothreitol or dithioerythritol, alkylating the thus-reduced interchain disulfide groups, and separating the thus-modified globulin from the nonproteanaceous reaction products.

Prior patents directed to selective elimination of aggregates by precipitation with polyethylene glycol include U.S. Pat. No. 3,763,135 to Shanbrom, et al.; U.S. Pat. No. 4,093,606 to Coval; U.S. Pat. No. 4,165,370 to Coval; and U.S. Pat. No. 4,276,283 to Eibl, et al.

Selective adsorption of aggregates by DEAE gels such as Sephadex ® C50 after Cohn fractionation are reported by Curling, J. M., et al., *Vox Sang* 33:97 (1977) and Suomela, H., et al., *Vox Sang* 33:37 (1977), U.S. Pat. No. 3,664,994 to Perper, U.S. Pat. No. 4,136,094 to Condie, U.S. Pat. No. 4,256,631 to Yokoo, et al., and U.S. Pat. No. 4,272,521 to Zuffi. Zuffi is of particular note in reporting on a process for removing existing and potential prekallikrein activator (PKA) from immune serum globulin using an ion exchange material to remove both the existing PKA and a kallikrein activatible precursor to PKA (factor XII).

Condie, U.S. Pat. No. 4,136,094 discloses a method for isolating and purifying IgG from animal blood plasma, the method involving an initial stabilization of the plasma by treatment with silica, followed by isolation of the IgG by an ion exchange chromatography step. The initial stabilization step comprises slurrying the plasma with fumed colloidal silica. Unfortunately, this aspect of the process results in the removal of a very substantial amount of IgG which adsorbs to activated silica used as described in Condie. In fact, utilizing a process wherein the fumed silica from the first phase is retreated for recovery of the adhered IgG, a maximum of 70% of the IgG in the starting plasma is recovered by Condie. Further, because the Condie process requires that the plasma be slurried with the fumed silica for one hour and mixed with the ion-exchange resin for forty minutes, the process does not readily lend itself to being operated in a continuous fashion, on a commercial scale.

Nakashima et al., U.S. Pat. No. 4,384,954, disclose a column for adsorption of blood proteins containing a blood inlet and a blood outlet, each with a filter, and a porous material packed between both the filters, the porous material having a mean pore diameter of 30–3,000 angstroms. The adsorption column is designed to eliminate specific blood proteins by selective adsorption. Included within the disclosure of this patent is the suggestion that the porous filtration media may be coated with a hydrophilic polymer, said hydrophilic polymer based on acrylic acid esters, polymers based on methacrylic acid esters, polymers based on acrylamide, polymers based on vinyl alcohol, polyvinylpyrrolidone, cellulose nitrate, and gelatin. The preferred coating polymers are copolymers of at least one acrylic or methacrylic acid ester with an epoxy group-containing polymerizable monomer. However, the Nakashima patent does not disclose a process for obtaining high purity injectable IgG, containing four subclasses of IgG and substantially devoid of other proteins, lipids, and the like.

Thus, in spite of the now well-recognized advantages of an intravenously injectable IgG and the plethora of investigative efforts to develop same, as evidenced by the vast quantity of patent and technical literature directed to the concept, none of the currently available IgG's have proven to be completely satisfactory. See Romer, et al., Vox Sang 42:62-73 (1982) and Romer, et al., Vox Sang 42:74-80 (1982).

Based on the above description of prior research regarding intravenously injectable IgG, it is apparent that isolation of IgG by fractionation procedures requires subsequent treatment in order to properly purify the product to eliminate aggregates resulting from the fractionation process. However, the various procedures for purification adopted to the present appear to introduce extraneous and undesirable artifacts of their own. PEG-treated products appear to be unsafe due to their elevated or very high PKA activity. The chemically modified preparations and enzyme-treated preparations contain split products or altered Fc portions. The method proposed by Condie, supra, has the enumerated disadvantages. Thus a need has continued to exist for an intravenous IgG preparation for clinical use which is essentially devoid of aggregates and dimers, contains no fragments, has an anti-complementary activity which conforms to the requirements for standard clinical use, has low levels of proteolytic enzymes such as PKA and kallikrein, is devoid of pyrogen and hepatitis B antigen (HBsAg), and has normal IgG subclass distribution, high product stability and long shelf life.

SUMMARY OF THE INVENTION

As mentioned previously, IgG has a high therapeutic value in the treatment of a variety of disorders. Additionally, the effectiveness of IgG is substantially improved where the IgG can be introduced intravenously rather than intramuscularly. However, current IgG preparations are not suitable for intravenous administration, the intravenous administration thereof frequently causing severe anaphylactic reactions which are attributed to the activation of the complement system by IgG containing polymeric or aggregated particles and fragments. Previous efforts to purify fractionated serum to obtain intravenously injectable IgG have proven unsatisfactory. With this as a background, applicants undertook to develop a new process for the preparation of intravenous IgG, said process not relying upon a fractionation technique for the initial step of the purification and recovery operation nor relying on chemical and/or enzymatic treatment. Their efforts have culminated in a process comprising a series of separation steps, said process resulting in the preparation of a highly pure intravenously injectable IgG product and high purity albumin, transferin and prothrombin complex by-products.

The process of the present invention, whereby intravenously injectable IgG is produced from animal plasma, comprises a series of sequential separations utilizing highly specific chromatographic support in at least a portion of the process. After a first dilution step to insolubilize lipids, animal plasma is subjected to a first filtration/adsorptive step to remove micron and submicron sized particulates, such as e.g. euglobulin, extraneous blood cells and fragments thereof, lipids, and lipimic colloids, and also activating complements such as prekallikrein. The filtrate from this separation process is passed to a next separation step wherein IgG is separated from other plasma-soluble large molecule proteins by ion-exchange chromatography, the IgG passing through the column, the other large molecule proteins remaining adsorbed on the column. The large molecule protein-free IgG from the previous step is passed to a next separation step whereby proteolytic enzymes are removed by affinity chromatography. The resulting IgG free of extraneous protein and proteolytic enzymes is then sterile filtered, lyophilized, and containerized.

BRIEF DESCRIPTION OF THE DRAWINGS

FIG. 13 is the HPLC pattern of IgG. 13(A) is prepared in accordance with this invention from the product of 13(B) and 13(C), which were intentionally dimerized by heating under the conditions indicated.

DESCRIPTION OF THE PREFERRED EMBODIMENTS

Outline of Description of Preferred Embodiments

Figure 1:
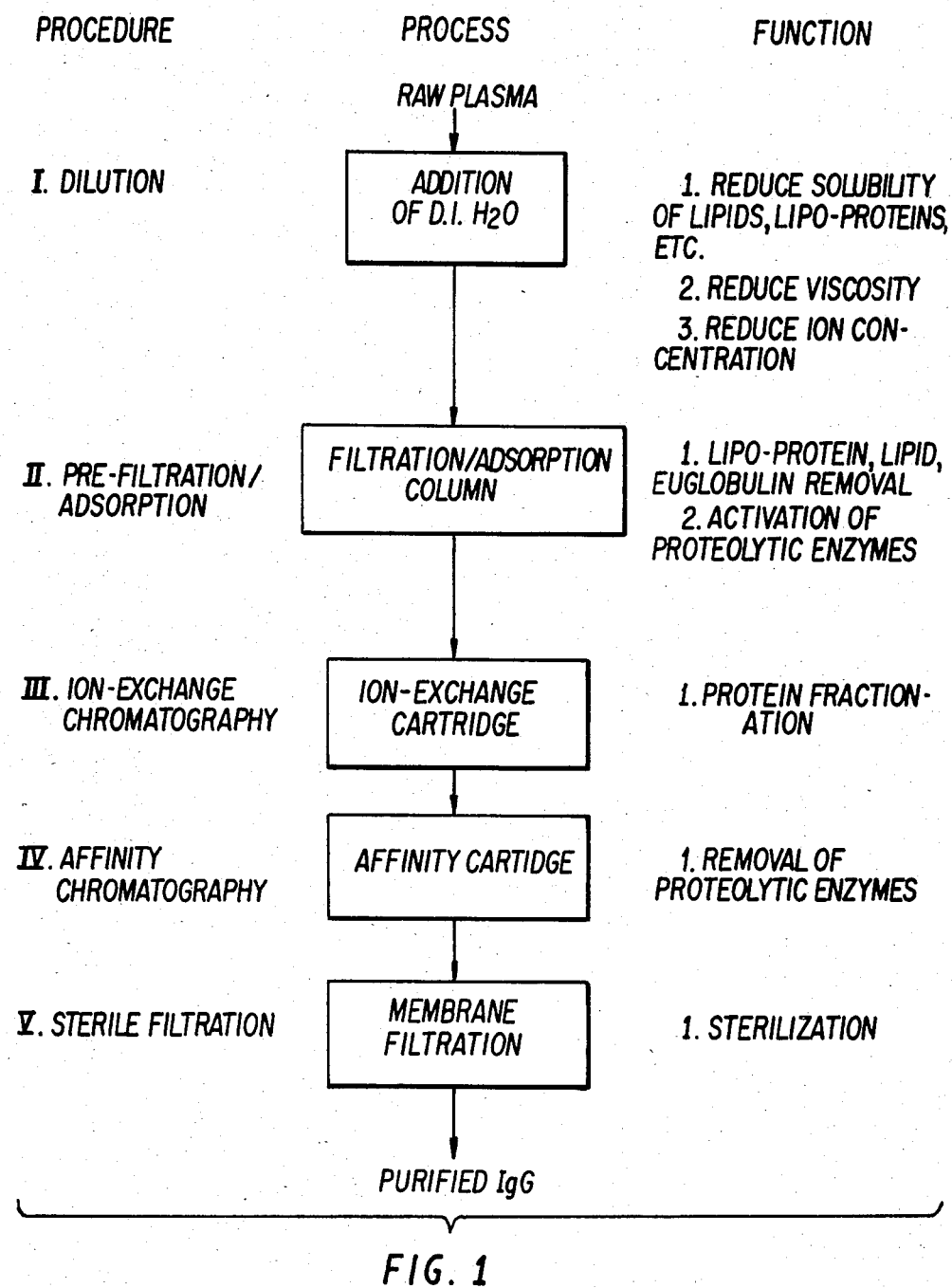
FIG. 1 is a block flow diagram of the sequential steps in the production of purified IgG.

I. Dilution of Plasma
II. Filtration/Adsorption
  A. Cartridge Configuration For Filtration/Adsorption
  B. Carbon Pads For Cartridge
  C. Silica Pads For Cartridge
III. Ion Exchange Chromatography Apparatus And Methodology For IgG Isolation And Purification
  A. Cartridge Configuration
  B. Matrix For Ion Exchange Chromatography
  B. Matrix For Ion Exchange Chromatography
    1. Configuration of Matrix
    2. Structure of Matrix
      a. Substrate of Ion-Exchange Matrix
      b. Covalently Bound Ion-Exchange Polymer
      c. The Synthetic Polymer-Modified Substrate
  C. Ion-Exchange Chromatographic Separation Of Plasma
IV. Affinity Chromatography of Partially Purified IgG
  A. The Enzymes In Partially Purified IgG
  B. Cartridge Configuration For Affinity Chromatography
  C. Matrix for Affinity Chromatography Of Partially Purified IgG
    1. Configuration of Matrix Or Stationary Phase For Affinity Chromatographic Separation Of Proteolytic Enzymes From Partially Purified IgG
    2. Structure Of Stationary Phase For Affinity Chromatographic Separation Of Proteolytic Enyzmes From Partially Purified IgG
      a. The Pre-Ligand Structure
      b. The Ligand and Its Coupling
  D. Enzyme Removal Using Affinity Matrix As Above
    1. Removal of Plasminogen Properties Of The Enzyme
    2. Affinity Matrix For Kallikrein Removal
V. Sterile Filtration Of Purified IgG
VI. Lyophilization And Packaging The starting material for the practice of the present invention is blood plasma or plasma fractions of human or non-human origin. Typical sources for the plasma include retroplacental blood from maternity wards and hospitals and excess blood and plasma which has become outdated. It is also possible to collect plasma by the so-called plasmapheres method whereby the blood, when being drawn, is mixed with a dextrose-sodium citrate-citric acid buffer which prevents the blood from coagulation. The blood corpuscles can be separated from the plasma by centrifuging and reinjected into the blood donor. In this way, the plasma constitutes the raw material for additional processing. In addition to human IgG, bovine IgG has substantial potential utility. In the cattle industry, newborn calves do not develop IgG antibodies for about 48 hours, leaving them vulnerable to a variety of diseases which create significant mortality among the newborn. Fresh or frozen human or other animal blood plasma or outdated and/or cryoprecipitate human or other animal plasma may be used as the starting material. Plasma, independent of whether it has been frozen, thawed, cryoprecipitated, re-frozen for transport, or Factor IX complex depleted may be treated, no matter what anticoagulants have been used at the time of blood or plasma collection. Serum, either in its original form or concentrated, may be used also.

I. Dilution Of Plasma

In a preferred embodiment of the present invention, frozen plasma, e.g. received from the local Red Cross is thawed and diluted with deionized water at a ratio of about 5:1 to 10:1 to decrease the solubility of lipids and then adjusted to a pH of approximately 6.0–6.8 with 6.3 being preferred, with 0.5 molar HCl. In addition to decreasing the solubility of lipids, the dilution also effectively lowers the ion content of the plasma, thereby increasing the effectiveness and efficiency of the ion-exchange step which follows. Any insoluble proteins and lipids precipitated out during the dilution may be removed by a simple filtering step. Following this first filtration, the serum is essentially free of large insoluble particulate matter.

The basic process of the present invention involves a sequential series of separation steps as represented by FIG. 1. Plasma which has been diluted with deionized water to precipitate out insoluble proteins and lipids is subjected to a single or multiple step prefiltration to remove insolubles, an ion-exchange chromatography for protein fractionation, an affinity chromatography for removal of proteolytic enzymes, and a final sterile filtration.

Figure 2:
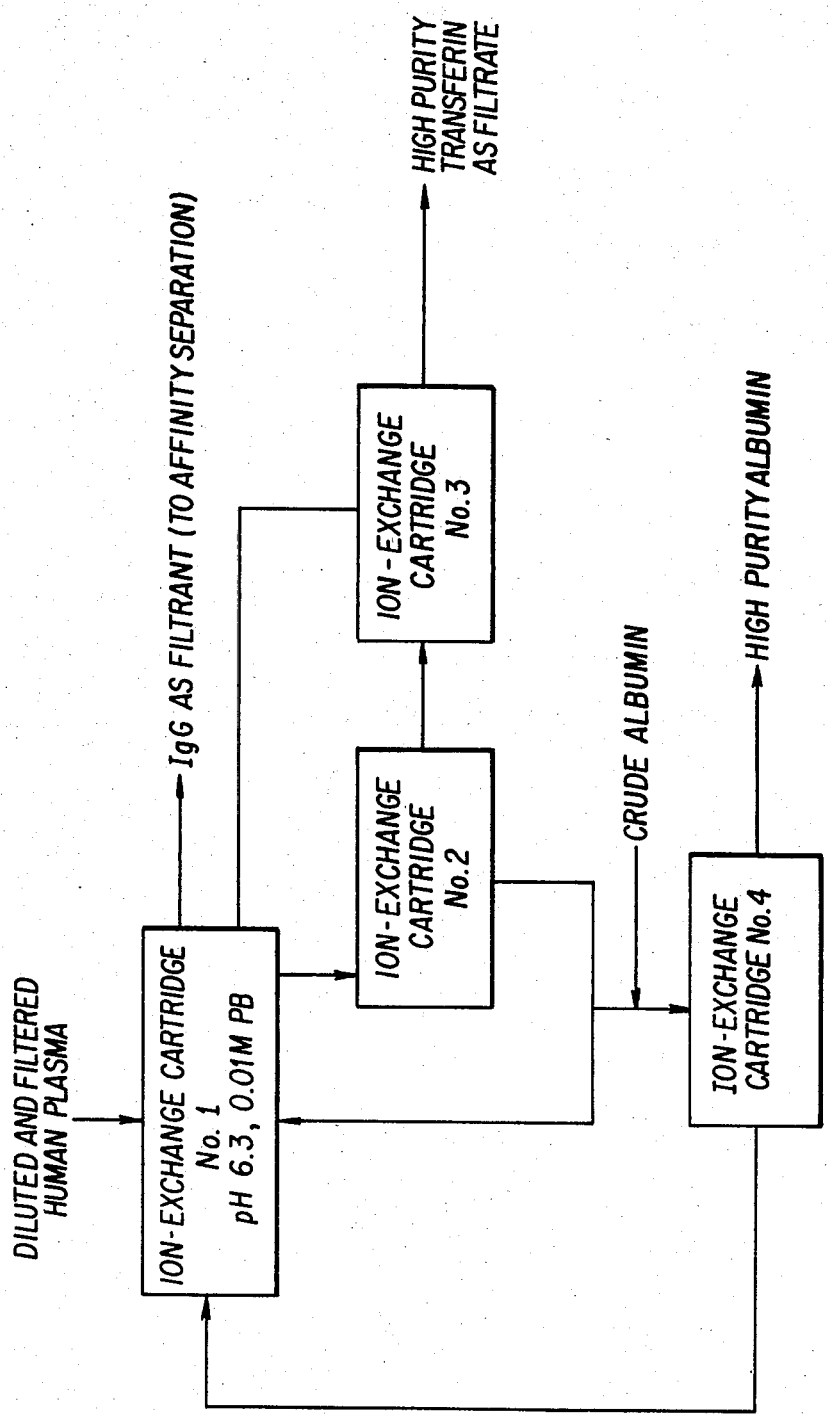
FIG. 2 is a block flow diagram of the sequential steps in the preferred process for high efficiency production of purified IgG and blood component by-products.

FIG. 2 depicts the preferred flow process for maximizing recovery efficiency and making available various of the other plasma components as by-products of the IgG purification. Referring to FIG. 2, prefiltered human plasma is passed through an ion-exchange column (No. 1), equilibrated at a pH of 6.3 with 0.01M PB (phosphate buffer), the IgG passing through the column, the other components remaining behind. The IgG stream then passes to an affinity chromatography column for further purification. Crude transferin is eluted from column 1 using a 30% monophosphate salt solution buffered with 0.01M PB. The eluate is passed through a second ion-exchange cartridge (No. 2), the effluent containing crude transferin passing into a third ion-exchange cartridge (No. 3) containing a cation exchanger equilibrated at pH 5.8. High purity transferin passes through cartridge No. 3, with residual IgG being adsorbed to the chromatographic media. The IgG is eluted from the No. 3 cartridge at pH 8.0 with acetate buffer and 0.5M salt and recycled through the ion-exchange cartridge No. 1 for recovery. Separately, crude albumin is eluted from cartridge No. 1 and cartridge No. 2 with 100% monophosphate salt and 0.01M PB, the two streams coinciding prior to introduction to cartridge No. 4, a cation-exchange chromatographic column equilibrated at pH 6.1. Optionally, this stream may first be treated to remove occluded transferin. High purity albumin passes through the cartridge No. 4 as effluent, with residual IgG and other impurities retained on the column. This column residue is eluted with the acetate buffer at pH 8.0 with 0.5M NaCl and recycled to cartridge No. 1, where the process begins anew.

II. Filtration/Adsorption

Returning now to FIG. 1, for this first step of pre-filtration to remove insoluble impurities, in a preferred embodiment, these insolubles are removed by passing the diluted plasma through a column or columns similar to those described in U.S. Pat. No. 4,384,957 to Crowder III, et al., the entire disclosure of which is incorporated by reference herein.

A. Cartridge Configuration For Filtration/Adsorption

Figure 3:
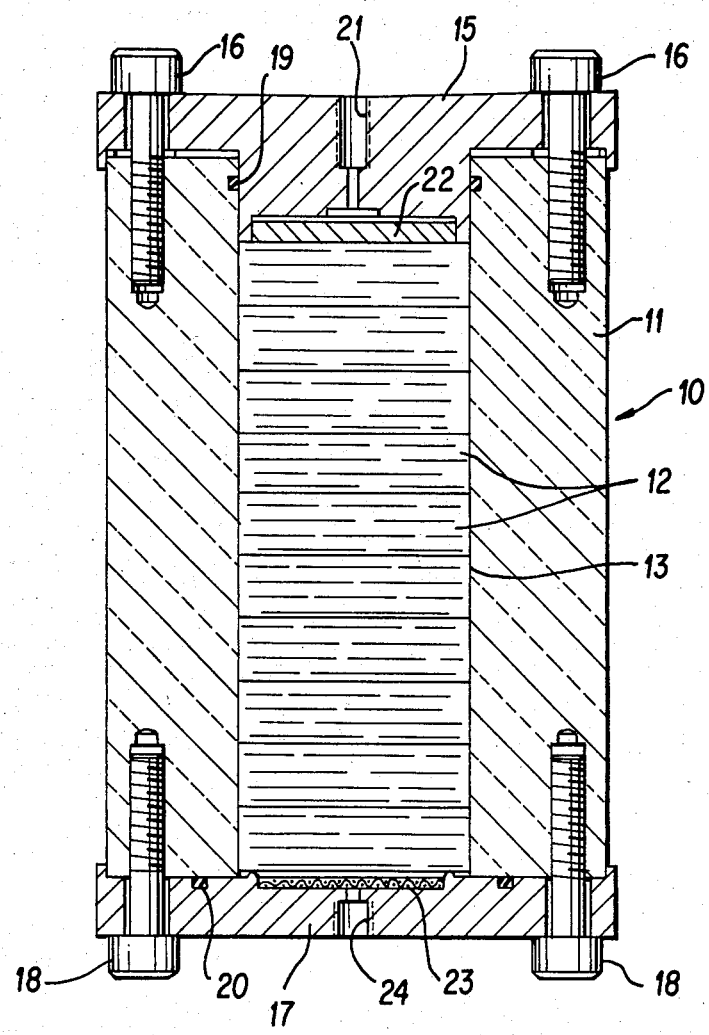
FIG. 3 is a cross-sectional view of a prefiltration/adsorption column used in this invention.

FIG. 3 represents a typical column for this preferred embodiment. The column (10) is a hollow cylinder (11) of circular cross-section which can be fabricated from any suitable material such as glass, steel, plexiglass and the like containing a number of discs of solid stationary phase elements (12). The edges (13) of the elements (12) form a fluid-tight seal with the interior wall of cylinder (11). The fluid-tight seal can be achieved in several ways. In one embodiment, the dimensions of the elements (12) and the interior of the cylinder (11) are such that the elements (12) are held firmly in place by a friction fit such that a pre-load compresses the elements. This requires very precise dimensional tolerances for both the interior wall of cylinder (11) and the elements (12). The individual elements (12) are inserted in the cylinder (11) usually with some mechanical aid such as a push-rod or piston. In a preferred embodiment which is suitable when an aqueous mobile phase is being passed through the column, the elements (12) are hydrophilic and swell somewhat upon contact with the mobile phase forming the required fluid-tight seal with the interior wall of cylinder (11). In this case, the dimensional tolerances of the interior surface of the cylinder and the elements (12) may not be as precise as in the case of a friction fit.

The column (10) includes an inlet cap (15) held in place by bolt (16) and an outlet cap (17) held in place with bolts (18). Inlet cap (15) is maintained in spaced relationship with cylinder (11) by spacer elements. Gasket rings (19) and (20) maintain an air-tight seal of caps (15) and (17) with cylinder (11). Inlet cap (15) is provided with an inlet orifice (21) for receiving liquid introduced into the column and inlet diffuser (22) for distributing the incoming liquid across the bore of the cylinder. Outlet cap (17) is provided with a support screen (23) to retain elements (12) within the column and an outlet orifice (24) through which the separated liquid is discharged.

The stationary phase (12) comprises a porous matrix of fiber having particulate immobilized therein, wherein at least one of said fiber or particulate is effective for separation of insoluble materials.

Preferred materials for this separation step include the activated carbon described in U.S. Pat. No. 4,404,285 to Hou and the fumed silica described in application Ser. No. 401,361 of Kenneth Hou et al., filed July 23, 1982 now U.S. Pat. No. 4,578,150 and application Ser. No. 347,360 of Hou et al., filed Feb. 9, 1982, now U.S. Pat. No. 4,511,473. The entire disclosures of each is incorporated by reference herein.

B. Carbon Pads For Cartridge

As described in U.S. Pat. No. 4,404,285, the preferred activated carbon filter/adsorbent is a composite sheet comprising a matrix of self-bonding fibers having carbon particles dispersed therein, with more than 90% of the carbon particles having an average diameter of less than 50 microns. The carbon-containing composites may be manufactured with different carbon loads and with different degrees of fiber refinement, thereby providing different, controllable degrees of porosity. The composite sheets are compounded with the activated carbon and from 10 to 50% of "other fiber", the term "other fiber" comprising any other fibrillated fiber such as cellulose, powdered carbon and polyethylene. Activation of the carbon takes place at 500°–2,000° C., with 10 to 90% of the carbon particles activated.

In the preferred filtration/adsorption column, composite sheets as described above are cut into discs and pads and packed into a cylindrical column, in stacked configuration, and in interference fit with the column wall. The method of manufacture of the carbon discs is fully described in the Hou patent.

The activated carbon, in addition to filtration/adsorption of lipids and the like, removes by adsorption any steroid and thyroid hormones present in the plasma.

C. Silica Pads For Cartridge

As described in the two Hou et al. applications to fumed silica mentioned above, the preferred fumed silica pads are self-supporting fibrous sheets containing high loads of microparticulates and long, self-bonding, structural fibers such as cellulose and the like. Preferably, the structural fibers comprise 50 to 90% of the sheet, the remainder (10–50%) being microparticulate fumed silica having a particle size less than 10 millimicrons.

The self-supporting silica matrix is made by vacuum-felting an aqueous slurry of fibers and particulate cast on a foraminous surface. After drying, the sheets may be cut into pads or discs and packed into a column such as that of FIG. 3.

In addition to delipidizing the plasma, fumed silica will also activate pre-kallikrein so that this proteolytic enzyme is eliminated in a subsequent chromatographic separation.

However, fumed silica has the disadvantage in that it is an adsorbant for IgG, as well as for proteolytic enzymes which have been activated, thereby reducing yields of IgG if used in excess. Accordingly, it is preferred that no more than 10% of the entire filtration/adsorption pad materials be fumed silica. In a more preferred embodiment, the fumed silica is replaced with silanized silica, the silanized silica still activating the pre-kallikrein but adsorbing essentially none of the IgG. This aspect is very important for the present invention where yields of 95% or more of the starting IgG are obtained. However, by using the cartridges as described above, with the fumed silica pads and activated carbon pads, high yield is still possible due to the unique pad configuration.

III. Ion-Exchange Apparatus And Methodology For IgG Isolation And Purification Following this plasma treatment step whereby micron and submicron sized particulate, lipids, hormones, etc. are removed from the plasma stream, the plasma is passed to a subsequent separation step whereby IgG is separated from the other proteins by ion-exchange chromatographic separation. This separation step represents one of the critical and highly inventive aspects to the present invention, combining a unique physical configuration of the chromatographic media and cartridge, a unique porosity control to the chromatographic media, and unique chemical separation and binding characteristics of the separation matrix.

A. Cartridge For Ion-Exchange Chromatography

In a preferred embodiment, the physical configuration of the chromatographic separation media comprises that disclosed in commonly assigned application Ser. No. 505,532, of Leeke, et al., filed June 17, 1983, and incorporated by reference herein. As disclosed therein, the solid stationary phase comprises a swellable fibrous matrix in sheet form. Preferably, the sheet is homogenous or substantially homogenous, which in effect means that the stationary phase is of a uniform or substantially uniform structure and/or composition transverse or axial to the radially flowing sample.

Figure 4:
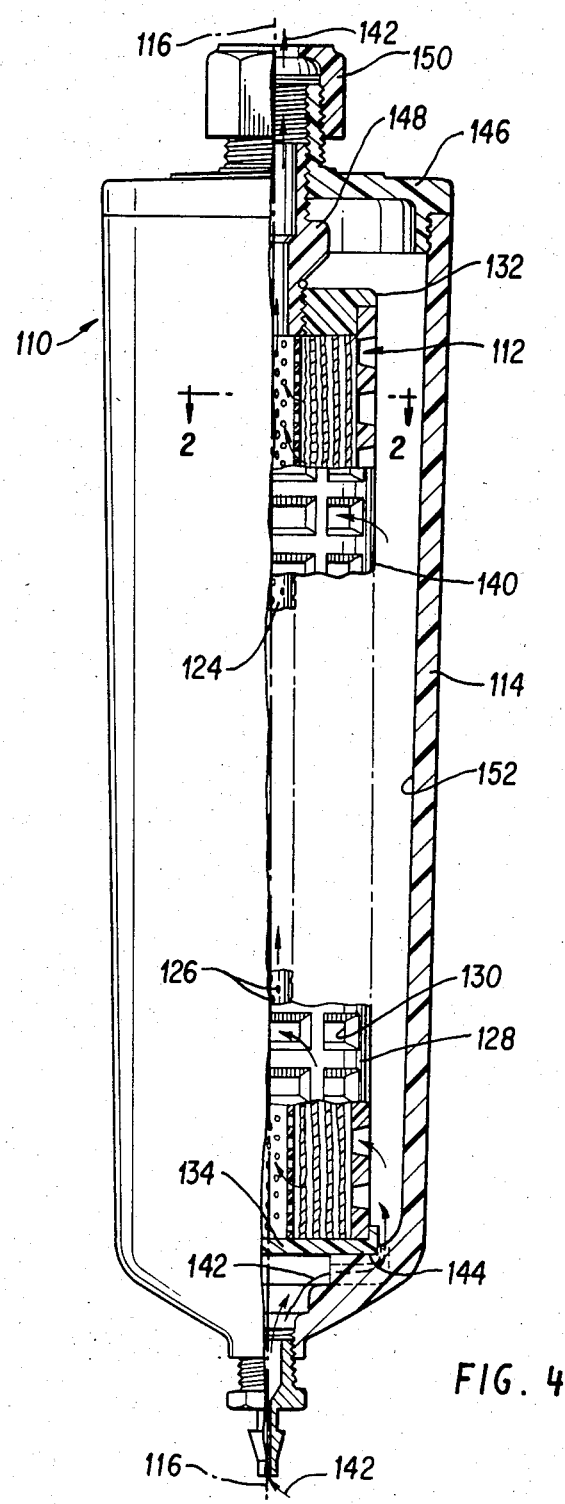
FIG. 4 is a partial sectional view of a side elevation of a preferred embodiment of the ion exchange or affinity chromatography column used in the present invention.
Figure 5:
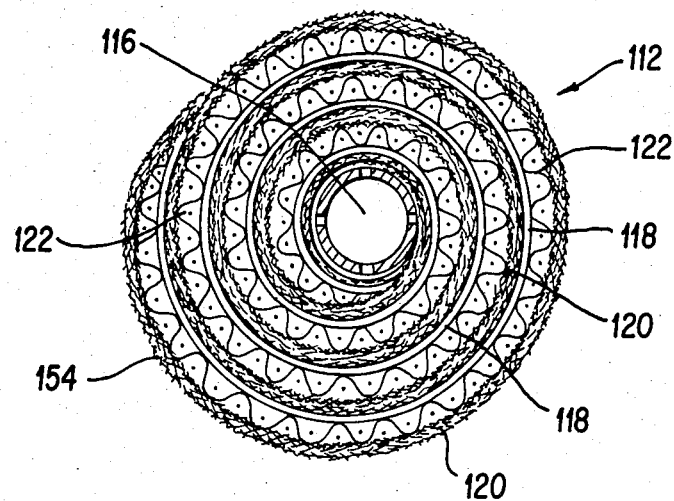
FIG. 5 is an enlarged cross-sectional view of FIG. 4, along line 2—2.
Figure 6:
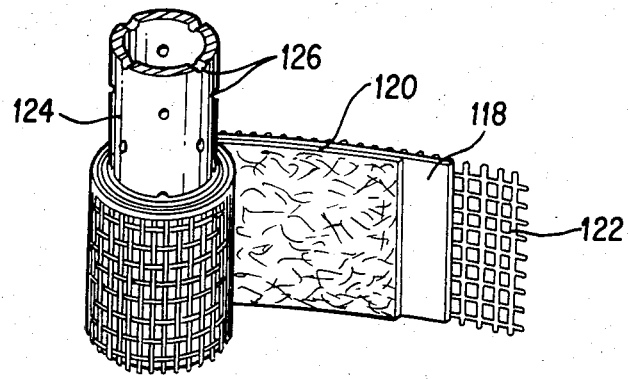
FIG. 6 is a perspective view of a portion of the solid stationary phase showing the spirally wound chromatographic media and spacer means therebetween.
Figure 7:
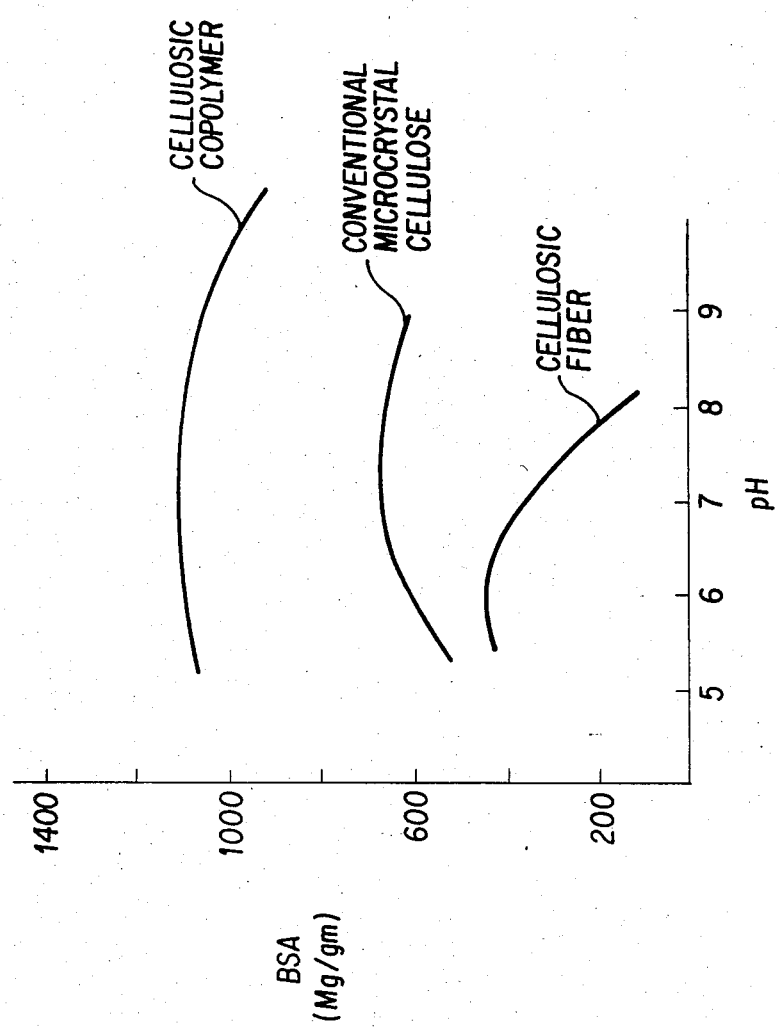
FIG. 7 is a graph comparing the BSA adsorption capacity of cellulose with the cellulose copolymer used for ion exchange in this invention.

Referring to the drawings, wherein like character references indicate like parts, FIGS. 4 through 6 depict a preferred embodiment of the chromatography column of this aspect of the invention. Referring to FIG. 4, the column, generally designated 110, is comprised of a cylindrical stationary phase 112, preferably in cartridge form, and a cylindrical chamber 114 which acts as a housing for stationary phase 112. The solid stationary phase 112 can be inserted into a glass, metal or polymeric tube or cylinder chamber 114 having a diameter somewhat larger than the external diameter of the stationary phase 112. Suitable fluid admission, collection and monitoring systems can also be employed with the column as in conventional analytical and preparative columns. The stationary phase 112 is positioned within the chamber 114 and preferably has a longitudinal axis 116 coaxial with the axis of the cylindrical chamber 114. Optionally, a plurality of cartridges 112 may be placed in a single housing in various configurations to effect parallel and/or series flow between the cartridges (not shown). See, for example, assignee's copending U.S. Ser. No. 611,682, filed May 18, 1984, to Daily, et al., the entire disclosure of which is incorporated herein. The solid stationary phase has chromatographic functionality and is effective for chromatographic separation. Referring to FIGS. 5 and 6, the stationary phase 112 is constructed of a swellable fibrous matrix, usually hydrophilic swellable, in sheet form 118 which is the active media for chromatographic separation. The chromatographic media in sheet form 118 is sandwiched between a scrim layer 120 of porous wettable fabric type material of, for example, polyester woven netting, and a non-woven mesh 122. The composite sheet of chromatography media 118, layer of scrim 120 and mesh 122, preferably non-woven, is spirally wound around a foraminous cylindrical core 124 having a longitudinal axis 116, to form a plurality of layers around the axis 116. The mesh 122, due to the openness and thickness thereof, acts as a spacer means between each layer of media 118 which permits the controlled expansion of the swellable media 118 without closing off the porous structure of the media and enhances the distribution of the sample flowing through the stationary phase 112. The cylindrical core 124 is provided with apertures 126 for the flow of sample into the open interior of the core 124.

Referring to FIG. 4, the wound composite sheet, 118, 120 and 122 and core 124 are then slipped into an outer cylindrical member 128 which is also provided with apertures 130. The ends of the cylinders are then capped by end caps 132 and 134. The end caps 132 and 134 are sealed by thermoplastic fusion to the outer cylindrical member 128 and also to the ends of the composite 118, 120 and 122. The fluid or sample 142 can thus flow radially from the outside to the interior of the solid stationary phase, i.e. the open interior of core 124, since the interior and exterior are completely separated by the solid stationary phase and sealed off by end caps 132 and 134.

The preformed end caps 132 and 134 are preferably applied to the cylindrical solid stationary phase 112 by heating an inside face of the thermoplastic end cap to a temperature sufficient to soften and preferably not liquify, a sufficient amount of the end cap to form a thermoplastic seal with the end of the cylinder 128. All of the edges of one end of the cylinder 128 are then embedded into the softened material. The softened material is then hardened, typically by ambient conditions, to form a thermoplastic sealing relationship between the sealing surface of the end caps 132 and 134, the cylinder 128 and the ends of the solid stationary phase 112 to form a leak-proof seal. Such methods of applying end caps are well known in the filtration art, see for example, assignee's PCT International Publication No. WO83/04186. Optionally, the end caps can be molded integrally in situ onto the solid stationary phase.

End caps of thermoplastic materials are preferred because of the ease of bonding, but it is also possible to use thermosetting resins in a thermoplastic, fusible or heat softenable stage of polymerization, until the bondings have been effected, after which the curing of the resin can be completed to produce a structure which can no longer be separated. Such a structure is autoclavable without danger of destroying the fluid-tight seal between the cylinder 128, the solid stationary phase 112 and the end caps 132 and 134. Thermoplastic resins having softening points sufficiently high so that they are not softened under sterilizing autoclaving conditions are preffered for biomedical use. Exemplary of the plastic materials which can be used are polyolefins.

Referring to FIG. 4, the preferred cartridge 140 has an end cap 134 on one end which does not open to the exterior of outer cylindrical member 128, but is closed off. This end cap 134 can nest on the bottom end wall 144 of cylindrical housing 114 while still permitting the flow of sample 142 into the chamber 114 around the outside of outer cylindrical chamber 128, or this lower end cap 134 of cartridge 140 is in spaced apart relationship from the bottom end wall 144 of cylindrical chamber 114, thus permitting the flow of sample 142 into the chamber 114.

The upper end of cartridge 140 has an end cap 132 which is in fluid communication with cylindrical core 124 thus permitting the flow of fluid from the center of cylindrical core 124 to the outside of end cap 132. A fitting 148 is inserted into end cap 132 so that it may engage the end wall 146 of cylindrical chamber 114. This fitting may be threaded (as shown) or separately or integrally molded with the end cap and having o-ring seals thereon. End wall 146 has thereon a threaded nipple 150 which permits the flow of treated sample 142 to pass from the core 124 through end cap 132, and end wall 146 into the process stream for additional processing. The end wall 146, and optionally end wall 144, may be threadedly attached to the wall 152 of cylindrical chamber 114 for easy access to the interior for cleaning and insertion of the cartridge 140.

However, it is also possible to utilize the ion-exchange matrix in a "stacked pad" configuration as described in Example 8 below.

B. Material For Ion-Exchange Chromatography

1. Configuration Of Matrix

In order to provide a chromatographic media matrix which is coherent and handleable, it is desirable that at least one of the components which go into forming the porous matrix be a long, self-bonding structural fiber. Such fiber gives the stationary phase sufficient structural integrity in both the wet "as formed" condition and in the final dry condition. Such a structure permits handling of the phase, in particular a sheet, during processing and at the time of its intended use. Preferably the sheets which form the chromatographic media are formed by vacuum felting an aqueous slurry of fibers. The sheets may also be pressure felted or felted from a non-aqueous slurry. The sheet shows a uniform high porosity, with excellent flow characteristics and is substantially homogenous. In general, the media can range in thicknesses of from about 4 mils to about 30 mils (dry), however, thicker or even thinner media may be utilized provided the sheet can be spirally wound to produce a cartridge which can perform as described herein. The media can swell to at least 25% this thickness, and generally greater, e.g. two to four times this thickness.

It is important when constructing the chromatography column of this invention that the chromatographic media used in the column be of uniform thickness throughout its length and width and that the media have a substantially uniform density throughout. It is preferred that the layer of media be substantially homogenous with respect to itself, however, for certain applications and material, it is to be understood that non-homogenous construction may be employed.

Since the solid stationary phase is intended in use to effect separation by maintaining a substantial pressure differential across the solid stationary phase, it is essential that the solid stationary phase have a sufficient degree of compressive strength to withstand deformation under such loads as may be imposed upon it. Such compressive strength must not only exist in the media itself but in the spacer means and the internal core upon which the chromatography media, or solid stationary phase is compressed.

The spacer means permits controlled expansion of the media and enhancement of the distribution of sample flowing through the stationary phase. The spacer means located between each layer of the swellable chromatographic media provide for the axial and the circumferential movement of the sample as the sample passes radially through the solid stationary phase. The spacer means function to uniformly control thickness and density of the chromatographic media during use. In addition, the spacer means can serve as a backing or support for the layer of chromatographic media. The latter aspect is particularly useful during the manufacturing phase.

It is preferred that the spacer means be composed of a material which is inert with respect to the chromatographic process. By inert, it is meant the material does not adversely affect the function of the solid stationary phase.

Referring to FIGS. 5 and 6, the spacer means may comprise two elements thereof, i.e., the scrim 120 and the mesh 122. The scrim material 120 functions to channel, to a certain extent, the sample flowing through the media and substantially evenly disperse the sample axially and circumferentially across the media. The mesh material provides spacing between the media to permit controlled expansion thereof to prevent the "cut-off" of flow therethrough by compression of the permeable media and also assists in distributing or channelling the sample flowing radially through the media both axially and circumferentially.

The scrim 120 is preferably a porous material which is wettable by the sample to maximize the distribution of sample during flow through the stationary phase. Such wettable scrims can, for example, be made of non-woven textiles, cloth, papers and similar materials. Suitable wettable scrims include polyester non-woven fibrous webs or woven webs, using mono-filaments or multi-filament yarn, the mono-filaments being preferred in terms of open structure and lower pressure drops, polyamides, and other relatively fibrous products, such as cellulose, regenerated cellulose, cellulose esters, glass fiber, and similar materials. Cellulosic and synthetic fiber filter papers may also be used as the scrim material, as well as perforated plastic sheets and open mesh expanded plastics. These latter more open type scrims merge, to a certain extent, into the mesh spacer material in function. It is conceivable that the function of the scrim and mesh may be combined into one type of material of proper wettability and pore structure to function in distributing the sample flowing through the stationary phase both axially and circumferentially while still permitting controlled expansion of the media to allow the passage of the sample therethrough to the next layer of media, for example, a porous compressible sponge-like material.

The mesh material is a more open type of material having openings ranging, for general guidance, from 1/16 inch to a ½ inch and is at least equivalent in thickness of the thickness of the media.

Referring to FIG. 5, after winding the chromatography media 118 on the core 124, the exterior surface 154 thereof is completely wrapped with the scrim material 120.

In operation, the sample is driven radially through the stationary phase and separated into distinct chromatographic fractions by the chromatographic media. The spacer means induce and permit circumferential and axial flow of this pattern as it moves through the column and therefore provides for improved resolution and utilization of the media's potential capacity.

Referring to FIG. 4, the sample is preferably introduced at the bottom of the column flowing to the outer surface of the solid stationary phase and then flowing radially inwardly through the layers of chromatographic media and spacer means into the perforated central tube 124 and is withdrawn centrally. It is apparent, from what has been set forth above, that the radial flow can also be caused to circulate in the opposite direction.

The cartridges decrease total processing time and when used with proper chromatographic media have excellent binding capacity. The cartridges may be used with standard type pumps or gravity feed and utilized, in the preferred mode, at from 5 to 50 psi. The cartridges of chromatographic media are totally enclosed and completely self-contained to ensure sterile conditions. Due to the fact that the solid phase cartridge is manufactured in a factory and assembled therein, each cartridge is virtually identical to the other, does not vary as in previously known columns, and eliminates the dependence upon packing expertise. Additionally, there is no premeasuring of chromatographic media, no media loss due to handling, no packing problems, no fines generation and removal within the column, and other problems associated with packing chromatographic cartridges. The column is simple to operate, and does not produce any channelling by passing or shifts in bed volume. The chromatographic cartridges allow scale up from milligram laboratory quantities to megagram production quantities. The cartridge provides rigidity and strength, and is particularly useful as a high flow medium pressure matrix and is highly suitable for large scale protein or non-protein purifications.

The cartridge made in spiral configuration formed by coiling alternate layers of the media and a vacuum material around the central spacer separates the successive layers of the matrix, thus preventing overlapping of the matrix layers and allowing the spacers for the matrix to either swell or shrink. The coiled cartridge contains a plurality of flow compartments which provides a large surface area for efficient bulk mass interchange with the substrate. Thus, the configuration offers a number of advantages which contribute to the overall inventive stature of this disclosure.

2. Structure of Matrix

Protein molecules are substantially larger in physical size than most other organic and inorganic compounds and require an elastic three-dimensional framework to accommodate migration through the support matrix in order to carry out ion exchange. At the same time, the support matrix must have sufficient rigidity to sustain the high flux of liquid flow. The balance of these two different requirements has presented substantial problems to the prior art. Applicants have previously solved this problem by providing a matrix with a proper pore size for easy penetration of protein molecules and adequate strength for maintaining flow rate at high capacity without collapse of the structure. Applicants have achieved this unique effect by selecting a combination of supporting material with a polymer or copolymer grafted thereto. Thus, these chromatographic materials comprise a support material which has been modified by grafting a polymer or copolymer thereto, the grafted polymer or copolymer containing the ion exchanging groups. Typical ion exchange materials are disclosed in commonly assigned co-pending application Ser. No. 576,448, filed Feb. 2, 1984, a continuation-in-part of application Ser. No. 466,114, filed Feb. 14, 1983; application Ser. No. 643,212 to Hou et al., filed Aug. 22, 1984 now abandoned, having the title "Modified Polypeptide Supports"; and application Ser. No. 643,613 to Hou et al., filed Aug. 22, 1984, having the title "Modified Siliceous Supports," each of which is incorporated by reference herein.

a. Substrate of Ion-Exchange Matrix

As mentioned above, the modified supports of the present invention comprise an organic synthetic polymer grafted to an insoluble carrier material. Typical carrier materials include polysaccharides, polypeptides, and silica.

The term "polysaccharide," as used in the specification and claims, is meant to include compounds made up of many—hundreds or even thousands—monosaccharide units per molecule. These units are held together by glycoside linkages. Their molecular weights are normally higher than about 5,000 and up into the millions of daltons. They are normally naturally occurring polymers, such as, for example, starch, glycogen, cellulose, gum arabic, agar and chitin. The polysaccharide should have one or more reactive hydroxy groups. It may be straight or branched chain. The most useful of the polysaccharides for the purposes of this invention is cellulose.

Cellulose is the preferred polysaccharide. By "cellulose" is intended to mean any of the convenient and commercially available forms of cellulose such as wood pulp, cotton, hemp, ramie, or regenerated forms such as rayon. There exists no criticality as to the selection of a suitable form of cellulose. Cellulose is a naturally occurring polysaccharide consisting of (1–4) linked glucose units. In the native state, adjacent cellulose chains are extensively hydrogen bonded, forming microcrystalline regions. These regions are interspersed by amorphous regions with less hydrogen bonding. Limited acid hydrolysis results in preferential loss of the amorphous regions and gives so-called microcrystalline cellulose. The cellulose useful in the present invention is either cellulose in the native state, or in the microcrystalline state. Also, cellulose derived from cotton linter is better than that derived from wood pulp, as the latter contains lignin.

Each anhydrous saccharide unit in a polysaccharide molecule may have three or more reactive hydroxy groups. Theoretically, all three or more can be substituted with the polymer. The product can be substituted with the polymer. The product from such reaction, however, would have a degree of substitution of three or more, which in the case of ion exchange materials, would render it soluble. Even at levels of substitution below those at which total water solubility occurs, such polysaccharide derivatives become unsuitable as chromatographic supports. Therefore, substitution of the polysaccharide is restricted to the more reactive centers of the amorphous region and is seldom carried out beyond the level of about 1 meg/gm of dry weight in fiber form. At this level of substitution, the native configuration of the polysaccharide structure is only slightly odified, and the low density nonuniform exchange sites are readily accessible to large biomolecules.

The term "polypeptide" as used in the specification and claims is meant to include compounds made up of many—tens, hundreds or even thousands—of amino acids linked through amide linkages (CONH) with elimination of water. A segment of such a chain is as follows:

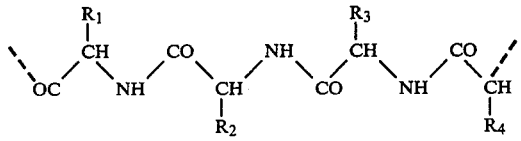

wherein $R_1$, $R_2$, $R_3$ and $R_4$ are typical amino acid residues.

The sequence of amino acids in the chain is of critical importance in the biological functioning of the polypeptide, and the chains may be relatively straight, or they may be coiled or helical. In the case of certain types of polypeptides, such as keratins, they are cross-linked by the disulphide bonds of cysteine. The polypeptide, however, may be biologically inert, such as a homopolyamino acid chain.

Proteins which are also polypeptides and can be coiled and folded into very complex special patterns and may be roughly classified into two groups on the basis of the extent of their coiling and folding. Those arranged as long linear molecules are called fibrous proteins. These fibrous proteins are relatively insoluble in water, salt solutions, and other aqueous media and make up important structural elements of the animal body. The fibrous proteins include collagen (the principal fibrous protein of skin, tendons, ligaments, cartilage, bone, the cornea of the eye, etc.), myosin (one of the chief proteins in muscle), keratin (the major protein in hair), and fibrin (a protein important in blood clotting).

The support material includes essentially all forms of insoluble polypeptides. However, the preferred polypeptides are the fibrous polypeptides. Among the fibrous polypeptides, keratin is the most perferred polypeptide for the purposes of this invention. Of the keratinous polypeptides, animal fiber such as wool and other types of epidermal hair are most preferred.

The term "wool", also a polypeptide substrate, is applied to the fibers from the fleece of the sheep and as such falls into the category of epidermal hair. The fiber structure is made of several layers of different types of keratin cells. The polypeptides comprising wool fiber are long peptide chains which are bridged by cysteine and salt linkage.

Where the substrate is a polypeptide such as wool, the final structure of the ion-exchange media comprises a polypeptide covalently modified at a multiplicity of sites along the chain, the sites modified with a synthetic or copolymer described in detail below.

The term "silica" is meant to include any and all siliceous materials in particulate form commonly used as carrier materials. Typically, these materials have a specific surface area of 5 to 1,500 m$^2$/g, a micropore diameter of 20–2,000 angstrom degrees, and a particle diameter of 1 micron to 1 millimeter. Typical silica materials include, but are not limited to, silicate containing clay minerals including talc, kaolinite, pyrophyllite, serpentine, smectite, montmorillonite, mica, and vermiculite; synthetic silicates such as silica gels, powders, porous glass, and those prepared by hydrolysis of calcium silicide or sodium silicate; and biogenic silicas such as kieselguhr and diatomaceous earth. These silica materials are characterized by surface hydroxy groups. However, cellulose represents the most preferred carrier material.

b. Covalently Bound Ion-Exchange Polymer

The carrier or substrate as described above, i.e. polysaccharide, polypeptide or silica, is modified by a synthetic polymer which is covalently bonded to the substrate through surface reactive groups of the substrate, for example, surface hydroxy groups of the polysaccharides, surface amino groups of the polypeptides, and surface hydroxy or SiOH groups of the silica. The polymer which modifies the substrate is either a homopolymer of a copolymer. The definition of the polymer as a homo- or copolymer depends on whether the polymerizable compounds making up the polymer are the same or different. In its most general form, the polymer may be a random, a block, or an alternating copolymer. An essential feature of the polymerizable compound is that it must contain a group capable of covalently bonding with the surface reactive group of the substrate and also contain either an ionizable chemical group or a group capable of transformation to an ionizable chemical group, said ionizable chemical group providing the ionic exchange. For purposes of the present invention, the group capable of covalently bonding to the surface reactive groups of the substrate is referred to as the "coupling group" and the ionizable chemical group or the group capable of being converted to an ionizable chemical group is referred to as the "ion exchange group." The coupling group-containing monomer is referred to as comonomer (a), while the ion exchange group-containing monomer is referred to as comonomer (b).

In one embodiment, the polymerizable compound (a) (also called comonomer (a)) may have a group capable of reacting with a hydroxy group of polysaccharide with the formation of a covalent bond. Such polymerizable compounds are defined for example in U.S. Pat. No. 4,070,348 to Kraemer et al., which is herein incorporated by reference. The chemical groups are capable of reacting with hydroxy groups at temperatures up to those at which the polysaccharide begins to decompose or depolymerize, e.g., 0° to 120° C., in aqueous solution and thereby form covalent bonds with the oxygen atoms of the hydroxy groups. Since water is always present in considerable excess with respect to the hydroxy groups, chemical groups which react spontaneously with water, such as, for example, isocyanate groups, are less suitable. Aqueous solutions comprise pure water or mixtures of water with one or more water miscible co-solvents, such as alcohols, ketones, and the like.

Hydroxy reactive groups of comonomer (a) are preferably activated carboxy groups such as are known from peptide chemistry or O-alkylating agents, such as alkyl halide or epoxide groups. Representatives of the O-alkylating comonomers are acrylic and methacrylic anhydrides, acrylolylmethacryloyl N-hydroxy succinimides, omega-iodo-alkyl esters of acrylic or methacrylic acid in which the alkyl group in general contains 2 to 6 carbon atoms, allyl chloride, chloromethylstyrene, chloroacetoxy ethyl methacrylate, and compounds having a glycidyl group. The latter are ethers or esters formed between a glycidyl alcohol and an unsaturated alcohol or unsaturated carboxylic acid, respectively. The glycidyl alcohols are aliphatic and cycloaliphatic alcohols and ether alcohols having from 3 to 18 carbon atoms which are esterified with an alpha,beta-unsaturated carboxylic acid, preferably acrylic or methacrylic acid, or are etherified with an olefinically or acetylenically unsaturated alcohol. Typical compounds are glycidyl acrylate (GA) and methacrylate; 4,5-epoxy-pentylacrylate; 4-(2,3-epoxy-propyl)-N-butylmethacrylate; 9,10-epoxy-steraylacrylate; 4-(2,3-epoxy-propyl)-cyclohexyl methacrylate; ethylene glycolmonoglycidyl ether-acrylate; and allyl glycidyl ether. Glycidyl acrylate and methacrylate are preferred, with glycidyl methacrylate (GMA) most preferred. In any event, comonomer (a) contains vinyl unsaturation to promote polymerization and/or copolymerization with other monomers.

If the active monomer units (a) are sensitive to hydroxy groups, and if they do not react with the polysaccharide offered, they may be transformed, in the presence of water, into hydrophilic carboxy or hydroxy groups. The activated groups are therefore present in the polymeric material in generally greater number than is necessary for the bonding with the polysaccharide.

In another embodiment, the polymerizable compound (a) may be one which does not react directly with hydroxy groups of the polysaccharide, but rather is covalently coupled to the polysaccharide indirectly, via a bridge compound. This is the case when the polysaccharide is first chemically activated as by oxidation, and reacted with a compound having, e.g., an epoxy group or a vinyl group, capable of reacting with an appropriate functionality of polymerizable comonomer (a).

Where the substrate to be modified is a polypeptide, then comonomer (a) contains vinyl unsaturation to promote polymerization and/or copolymerization and also contains a coupling group which is capable of covalently bonding to the polypeptide chain through the amino groups of the polypeptide chain. Typical groups capable of so reacting include glycidyl groups and N-methylol groups. Typical monomers containing glycidyl groups are those mentioned above, with glycidyl acrylate and methacrylate again preferred, glycidyl methacrylate being most preferred. Typical monomers containing N-methylol groups include N-acrylamide.

Where the substrate to be modified is silica or a siliceous material, then comonomer (a) contains both vinyl unsaturation for polymerization purposes and a group capable of coupling to the hydroxy or SiOH surface groups. Typical monomers include the glycidyl-group containing monomers mentioned above. Again, glycidyl acrylate and methacrylate are preferred.

The polymerizable comonomer (b) will vary depending on the ultimate use of the carrier material in this invention. As an ion exchange chromatographic material, following the prefiltration, the comonomer (b) may contain any of the well known ionizable chemical groups or precursors thereof such as compounds containing a vinyl or vinylidine group and a carboxylic acid, a carboxylate salt, a carboxylate ester (preferably having 1 to 6 carbon atoms), a carboxylic acid amide, a secondary or a tertiary amine, a quaternary ammonium, a sulfonic acid, a sulfonic acid ester, a sulfonamide, a phosphoric or phosphonic acid, or a phosphoramide or phosphonamide group.

When comonomer (b) carries the precursor of a material having ion exchange properties, the ion exchangable group itself can be obtained by unmasking, such as for example, by selective hydrolysis of an anhydride, ester or amide, of salt formation with an appropriate mono-, di- or trivalent alkaline or alkaline earth metal, as is otherwise well known in the art. Preferred ion exchange functionalities for comonomer (b) are aminoethyl, carboxymethyl, carboxyethyl, citrate, dimethylaminoethyl, diethylaminoethyl, ecteola (mixed amines), guanido ethyl, phosphonic acid, p-aminobenzyl, polyethylene imine, sulphoethyl, sulphomethyl, triethylaminoethyl, or chelating groups such as —N(CH$_2$CO$_2$H)$_2$. Preferred anion exchange comonomers are diethylaminoethyl acrylate (DEAEA) and methacrylate (DEAEMA). Where greater hydrophilicity is a consideration, dimethylaminoethyl acrylate (DMAEA) and methacrylate (DMAEMA) are particularly useful.

However, for the purposes of the present invention wherein this ion-exchange step of the process separates out large molecule proteins, DEAEMA is the preferred comonomer (b) and the GMA-DEAEMA copolymer is the preferred ion-exchange copolymer for anion exchange. For cation exchange, the preferred exchange polymer is GMA modified with Na$_2$SO$_3$ or methacrylic acid in accordance with Examples 3 and 4 respectively, below.

The average molecular weight of the substrate-modifying polymer is dependent on the number of monomers present therein. It is required to have at least a sufficient amount of comonomer (a) so as to be able to form covalent attachment throughout the substrate surface. The amount of comonomer (b) cannot be too small, since otherwise the exchange capacity, or the anchoring/interacting capacity is negligible. The amount of comonomers (b) can neither be too high, since this would cause great difficulty in the reaction between the reactive groups of comonomer (a) and the substrate. Preferably, the substrate-modifying copolymer carries anywhere between 1 and 500 units (a) plus (b), most preferably between 20 and 100 units. This corresponds to molecular weights of between about 1,000 and 1,000,000, preferably between 5,000 and 20,000.

Other neutral comonomers (c), different than supra, can also be added to the polymer, if desired. These comonomers may be polymerizable unsaturated compounds carrying neutral chemical groups such as hydroxy groups, amide groups, alkyl groups, aryl groups and the like. Preferred among comonomers (c) are C$_1$-C$_6$ alkyl acrylates or methacrylates, or the corresponding hydroxy alkyl acrylates or alkacrylates. The function of comonomers (c) may be to increase the presence of hydrophobic or hydrophilic residues in the polymers, so as to provide a desired balance of hydrophilic and hydrophobic groups, if necessary.

The minimum ratio of comonomer (a) to total comonomer content is important. The synthetic polymer should have a sufficient amount of comonomer (a) to permit substantial covalent coupling of the polymer to the substrate. If too little comonomer (a) is present in the polymer, then grafting becomes difficult, if not impossible. Generally, about 4–20, preferably 5–10% by weight of comonomer (a) relative to the total of (a) plus (b) (and (c) if any is present is needed. Amounts of about 0.5 to 1 or 2% by weight appear merely to crosslink the polymer, without substantial grafting onto the substrate.

The upper limit of comonomer (a) in the polymer can be varied up to 99.9% by weight, depending on the desired amount of rigidity, functionality and hydrophilicity. Increasing the amount of comonomer (a) too much above 15 to 20% by weight, however, decreases the porosity. Large molecules then have difficulty in gaining full access to the functional groups in comonomer (b). It is preferred to have a predominance of comonomer (b) over comonomer (a). Comonomer (c) may be present in an amount of up to 20% by weight of the total (a) plus (b) plus (c).

The weight ratio of substrate to the modifying polymer is freely adjustable, and varies from 0.1 to 5 weight parts of polymer to parts by weight of the substrate.

When comonomer (b) carries ionizable chemical groups capable of providing ion exchange capacity, it is found that unless some degree of crosslinking is provided, the flexibility of the material in solution tends to favor the formation of micelle-type aggregates and slow loss of capacity. Therefore, it is a preferred mode of the invention to provide polymeric crosslinking for these types of modified substrates. Crosslinking can be provided either by incorporating into the polymerization recipe a small amount of polyunsaturated comonomer having at least two polymerizable alpha, beta-carbon double bonds, such as for example mono- and polyethylene glycol dimethacrylates and diacrylates (with the polyethylene glycol residue containing up to 6 ethylene groups), ethylene dimethacrylate, ethylene diacrylate, tetramethylene dimethacrylate, tetraethylene diacrylate, divinylbenzene, triallyl cyanurate, methylene-bis-acrylamide or -bis-methacrylamide, and the like.

Another type of crosslinking agent is particularly applicable to copolymers made from an aminoalkyl comonomer (b). Because of the presence of a free pair of electrons on the aminoalkyl nitrogen atoms, crosslinking can be carried out with such bifunctional reagents as would react with nitrogen-free electron pairs. Among these are the diacyl halides, such as Hal-CO-$(CH_2)_n$-CO-Hal and Hal-CO-phenyl-CO-Hal, or the alkyl or aryl dihalides, such as Hal-$(CH_2)_n$-Hal and Hal-phenyl-Hal, wherein Hal is a halide such as chloride, bromide or iodide, and n may be anywhere between 2 and 12. Other bifunctional reagents capable of reaction with nitrogen atoms can also be used, such as diepoxide compounds. The advantage of these bifunctional reagents is that they simultaneously crosslink the copolymer, while also providing a cationic charge at the nitrogen centers, thereby ionizing the material.

The amount of crosslinking agent is best determined empirically. It is to be considered sufficient when the polymer preserves the ion exchange capacity at a constant value over time, yet would be too high if swelling is prevented, and too much rigidity is obtained in the final materials. Ideally, an amount of crosslinking agent between 1 to 20 mole percent of the synthetic polymer units is sufficient.

The modified substrate materials are preferably in fibrous form after the modification, and can be formed into a self-supporting fibrous matrix, such as a fibrous sheet, with ion exchange properties. The modified fibrous media can also incorporate unmodified fibers of various different sizes, and, in addition, can also incorporate modified or unmodified particulate material.

c. The Synthetic Polymer Modified Substrate

The fibrous media comprises a porous matrix of fiber wherein, the fiber is effective for molecular or ionic separations or molecular reactions. The matrix is substantially homogeneous with respect to each component. When a particulate is present, it is preferred to modify it so that it is also effective for molecular or ionic separations of the IgG and by-product from the serum. Such a particulate should be contained in the fibrous phase in an amount effective to achieve the desired separations or reactions. The overall media is substantially inert and dimensionally stable.

Another embodiment of the invention, which may also be coupled with the aforementioned polypeptides and polysaccharides is an unrefined structural fiber which assists in providing sheets of sufficient structural integrity in both the wet "as formed" condition, and in the final dry condition, for incorporation into the cartridge, and also allows handling during processing as well as suitability for the plasma separation. Such fibers are typically relatively large, with commercially available diameters in the range of 6 to 60 micrometers. Wood pulp can also be used and has fiber diameters ranging from 15 to 25 micrometers, and fiber lengths of about 0.85 to about 6.5 mm. The unrefined self-bonding structural fibers typically have a Canadian Standard Freeness of +400 to +800 ml. Canadian Standard Freeness is described in full in U.S. Pat. No. 4,309,247, incorporated by reference herein. These long self-bonding fibers may constitute greater than 50% of the fibrous media, by weight, preferably 60–100% of the fibrous media, most preferably 100%. Optionally, a minor portion of cellulose pulp which has been refined to a Canadian Standard Freeness of between +100 and −600 ml may be incorporated with a major portion of the normally dimensioned cellulose pulp (+400 to +800 ml). In particular, from about 1 to about 20% of the refined pulp and about 50% to about 90% of the unrefined cellulose may be contained in the matrix.

C. Ion-Exchange Chromatographic Separation Of Plasma

While the above recite many embodiments which are encompassed by the present invention for effecting the ion exchange phase of the process wherein IgG is separated from other proteins in the plasma, the preferred ion exchange material for chromatographic separation is that material wherein the substrate is a cellulosic material and the modifying polymer is a copolymer of glycidyl methacrylate (GMA) and diethylaminoethylmethacrylate (DEAEMA). By selecting the proper size of cellulosic supporting material and controlling crosslinking by the amount of GMA incorporated in the graft polymer, one can engineer a matrix having proper pore size for easy penetration of protein molecules and adequate strength to permit flow rates required for industrial scale operation.

Selective separation of IgG from plasma by ion exchange has been used in the past for small scale operation. Typical separation techniques involve the use of DEAE attached directly to various types of solid phase matrices such as polystyrene, Spackman, et al., *Anal. Biochem,* 30: 1190 (1958); cellulose, Baumstark, et al., *Arch. Biochem. Biophys.* 108: 514 (1964); dextran gels, Heystek, et al., *Vox Sang* 25: 113 (1973); and crosslinked agarose, Curling, et al., *Vox Sang* 33: 97 (1977). However, one of these prior art ion exchange materials have proved satisfactory for operating procedure required by the large scale application and purity levels of the present invention. In contrast, the present invention has proven to be superior in the following manner:

(1) physically, the cartridge design containing the ion exchange media eliminates the channelling problems that exist in packed column methods, leading to high resolution and separation of the serum;

(2) dimensional and chemical stability of the dry paper structure reduces the time required for equilibration and elution, and makes the process economically attractive, permitting the processing of large amounts of serum in a short time;

(3) the minimal non-specific adsorption of protein in the cartridge enables one to achieve high IgG yield for maximum recovery;

(4) the hydrophilic nature of the cellulosic substrate provides an environment which does not contribute to the denaturation of the IgG molecules, while at the same time the mild hydrophobicity induced by the grafted vinyl polymer makes the modified substrate effective as a lipoprotein adsorbent for plasma clarification;

(5) the accessibility of the charge groups located in the matrix makes the peripheral orientation of the charged groups highly efficient for ion exchange, the resulting product exhibiting a high protein adsorption capacity (see FIG. 6);

(6) the particular pore configuration of the matrix provides macropores adequate for IgG migration and yet still small enough to remove the larger molecules such as fibrinogen, at the same time providing high efficiency for removal of the aggregates and dimers of IgG;

(7) by eliminating the fractionation step of the Cohn fractionation process, denaturation of protein by ethanol is eliminated, thereby providing for a high product yield and simplicity of operation, at the same time avoiding the denaturing effect on some proteins which is caused by the structural alterations and avoiding as well the pro-enzyme activation or formation of new antigenic determinants.

Previous efforts at fractionating plasma to produce highly purified intravenously injectable IgG utilizing variations of the Cohn fractionation technique result in the production of aggregates or splits of IgG molecules as discussed above. The plasma fractionation technique of the present invention is based on the different isoelectric points of the various plasma proteins (see FIG. 8). By equilibrating the ion exchange cartridge at a pH of 6.3–6.8, IgG will pass through the column as filtrant, with the other components, having isoelectric points lower than IgG, adsorbed in the cartridge. Those components having a higher isoelectric point will pass through the column with the IgG.

As mentioned previously, one additional advantage of the present technique permits these other proteins to be subsequently eluted out by pH and salt gradient procedures, thereby making possible their recovery as well. Referring again to FIG. 2, it may be seen that IgG pass through a GMA-DEAEMA cartridge equilibrated at pH 6.3 with 0.01M PB, with transferin retained on the column. Subsequently, the transferin may be eluted from column No. 1 using a 0.01M PB buffer solution containing 30% of monophosphate salt. High purity transferin may be recovered from the GMA-DEAEMA cartridge No. 2 by passing this same material through cartridge No. 3, equilibrated at pH 5.9. Specific parameters and results are reported at Example 19 below.

Similarly, high purity albumin may be recovered by eluting the original cartridge No. 1 with 0.01M PB and 100% monophosphate salt by passing the eluate through a GMA cartridge equilibrated at pH 4.8, cartridge No. 4 in FIG. 2. Additionally, any albumin eluted in the recovery of transferin may be eluted from cartridge No. 2 using a 100% monophosphate salt, this stream passing into cartridge No. 4 as well. Specific data and conditions are reported below at Example 18.

IV. Affinity Chromatographic Separation Of Partially Purified IgG

A. The Enzymes In Partially Purified IgG

The filtrate from the ion chromatography step above is essentially free of proteins other than IgG. Albumin, IgM, IgA, transferin and the like have been left behind, adsorbed to the substrate in the ion exchange column or cartridge. Additionally, the dimers and aggregates of IgG, so troublesome in terms of anti-complementary activity, have been removed as well. However, the serum at this point still contains other problem impurities such as proteolytic enzymes. The two major proteolytic enzymes in human plasma are plasmin (about 12 mg/dl in normal human plasma) and kallikrein (about 10 mg/dl in normal human plasma). The biological activity of these enzymes include their ability to fragment IgG and to cause increased blood vessel capillary permeability. Additionally, other enzymic contaminants such as pre-kallikrein activator (PKA) and the proenzyme plasminogen are also found, although a part of the plasminogen may have been previously removed.

When preparations containing PKA are given intravenously, the side reactions may include flushing, chest pain, and hypotension due to PKA-induced generation of bradykinin in the recipient. Therefore, an improved intravenous IgG would be characterized by the absence or extreme low levels of these proteolytic enzymes such as plasmin and kallikrein and their precursors, plasminogen and PKA. While U.S. Pat. No. 4,305,870 to Liu et al. has suggested the removal of residual exogenous PKA activity by bentonite adsorption, this approach dramatically reduces the yield of IgG. Thus, an important aspect of the present invention involves the use of affinity columns or cartridges for specific removal of proteolytic enzymes in plasma. In our tests, it was noted, for example, that kallikrein activity jumped from 11.0 mu/ml in the original serum to 528 mu/ml after passing the serum through the ion exchange matrix above. One possible explanation for this jump in kallikrein activity is that the enzymic activity in plasma is controlled by the balance between the enzyme activators and enzyme inhibitors. In the presence of inhibitors, the enzymic activity may not be easily detected. The sudden jump of enzymic activity in IgG after being passed through the ion exchange matrix in our process is probably due to an inadvertent removal of the specific inhibitors which inhibit its activity.

PKA is a single chain glycoprotein with a molecular weight of approximately 82,000. The isoelectric point is 7.7. Several enzymes catalyze the activation of plasma PKA to kallikrein, including trypsin, factor XIa fragments, and factor XII in the presence of certain negatively charged surfaces. The conversion of PKA to kallikrein involves the hydrolysis of an internal peptide bond resulting in a two chain structure held together by disulfide bonds.

B. Cartridge Configuration For Affinity Chromatography

In the affinity separation step wherein proteolytic enzymes such as kallikrein are removed from the partially purified plasma, in the preferred embodiment, the affinity matrix (described in detail below) is preferably contained in a cartridge configured as that in FIGS. 4–6 and described in detail supra. This preferred cartridge configuration is essentially that utilized in the ion-exchange chromatography described above, only the stationary phase or matrix being different.

The advantages attendant to the use of the cartridge so configured are essentially those same advantages described above for the ion-exchange cartridge, i.e., a plurality of flow compartments for large surface area, simplicity of operation, lack of handling difficulties, no packing difficulties, no channelling, etc. Again, the cartridge configuration itself is a preferred embodiment contributing to the inventiveness of the process. Additionally, as with the ion-exchange cartridge, the cartridge configuration is responsible for the high processing capacity for the method, this high processing capacity contributing to the overall efficiency of the operation. However, it is within the scope of this invention to utilize a conventional "packed" column as well. In that case, the stationary phase may be formed in a sheet and cut into appropriately sized discs.

C. Matrix For Affinity Chromatography Of Partially Purified IgG

1. Configuration Of Matrix Or Stationary Phase For Affinity Chromatographic Separation As in the ion-exchange cartridge described above, the matrix for affinity separation, in its preferred embodiment, is as described in FIGS. 4–6 with regard to its physical configuration. Essentially, the cartridge stationary phase or matrix is made in spiral configuration formed by coiling alternate layers of the media and a vacuum spacer around the central spacer, thereby separating successive layers of the stationary phase. By so configuring the stationary phase, overlap of the stationary phases is eliminated, the spacers then able to swell or shrink in response to various conditions. In this manner, the cartridge contains a large surface are for efficient bulk mass interchange with the stationary phase.

2. Structure Of Stationary Phase For Affinity Chromatographic Separation a. The Pre-Ligand Structure

In the practice of the present invention, where animal plasma, such as human plasma, is processed to recover high purity IgG and by-product, the affinity matrix is produced by grafting a polymeric carrier onto a substrate and then coupling an affinity ligand to the grafted, covalently bound synthetic polymer. This pre-coupled structure is referred to below as the pre-ligand structure. Suitable substrates include the substrates mentioned above for producing the ion exchange chromatography substrates, i.e. polysaccharides such as cellulose, polypeptides, and silica. Again, cellulose is the preferred substrate material for use in this phase of the plasma separation.

The polymer which is grafted to the substrate may contain functional groups which act as precursor groups for various types of functional groups such as amine and thio. This type of modification provides a means for subsequent derivatization to meet specific needs. Typical monomers include ethylenically unsaturated oxirane-containing monomers such as glycidyl acrylate and methacrylate, ethylenically unsaturated hydroxy-containing monomers such as hydroxyethylmethacrylate, and ethylenically unsaturated amide group-containing monomers such as acrylamide. Glycidyl methacrylate (GMA) the glycidyl acrylate (GA) are the preferred grafting monomers.

An important factor in the preparation of a satisfactory affinity matrix for the enzyme removal phase of the process is controlling the pores in the network such that even after ligand coupling there is sufficient space left for the enzyme protein molecules to freely penetrate for ligand binding. However, requirements for such large pore size frequently cause mechanical stability problems. Currently available commercial products sold as affinity matrices rely on a carefully controlled degree of crosslinking to provide structural rigidity. However, these lightly crosslinked materials are extremely fragile, frequently degrading under even conventional stirring techniques. While increased physical stability may be achieved by increasing the crosslinking, the increased linking decreases the porosity of the material.

In one embodiment of the present invention, this problem of balancing the requirements of structural rigidity and porosity are accomplished with a two step interpenetrating network wherein cellulose or some other natural polymer provides a three-dimensional skeleton within and around which a second network of acrylic polymer is formed. The cellulosic or other natural polymer substrate provides the necessary rigidity, permitting the acrylic polymer to be only lightly cross-linked, this lightly crosslinked polymer possessing the required chemical and porosity properties. Under polymerization conditions similar to those of Example 3, crosslinking occurs.

The synthetic polymer may be formed utilizing any of the polymerization techniques conventional in the art. Suspension polymerization is a preferred polymerization technique, the monomer suspended and maintained by continuous stirring of the reaction mixture, optionally with the use of surfactants. A free radical initiator is employed which dissolves in the monomer phase and polymerization is achieved by a thermal fragmentation of the catalyst. Prior to completion of the polymerization, reaction conditions are altered to facilitate the coupling reaction whereby the polymerization product hydrocarbon chains, with attendant functional groups attached, are then grafted to the natural polymer substrate. During this latter phase of the polymerization, both polymerization and coupling proceeds simultaneously.

GMA grafted to cellulose represents the preferred affinity matrix. GMA provides three functions, the oxirane groups of the GMA monomer providing covalent coupling with the surface hydroxy groups of the cellulose, these same oxirane groups providing cross-linking capability for the synthetic polymer network, and the remaining oxirane groups serving for subsequent ligand coupling. See FIG. 9 for a representational drawing of a GMA-modified cellulose.

The following is a description of the physical and chemical characteristics of the GMA-cellulose affinity matrix:

1. Mechanical Rigidity—Cellulose fibers provide good structural strength as a solid support member. These fibers are further strengthened by the strong hydrogen bonding force between the polysaccharide units of the cellulosic fibers, additional strength provided by the highly crystalline structure. Additional mechanical rigidity is provided by crosslinking which occurs between the cellulose and the synthetic polymer.

2. Macroporosity—Careful selection of fiber diameter, length, degree of fiberization and degree of cross-linking provides for a high degree of control of macroporosity.

3. Hydrophilicity—The hydroxyl groups in the cellulosic structure provide for a high degree of hydrophilicity. Further, oxidation of the glycidyl groups of the GMA polymer to diols or copolymerization of the latter with a hydroxyl-containing monomer further add to the hydrophilic character of the matrix.

4. Chemical Resistivity—Cellulose has a low solubility in a product solvent; further, solvent resistance is provided by crosslinking the glycidyl groups of the GMA polymer with each other and with the hydroxy groups of the cellulose.

5. Structural Integrity—Swelling and shrinking of the matrix is negligibly small due to the grafted crosslinkable monomer, further stability being provided by additional crosslinking with a bifunctional monomer.

6. Low Non-Specific Adsorption—The grafting process further purifies the cellulosic raw materials, decreasing the number of available sites for non-specific binding.

7. Chemical Reactivity—As much as a 200% weight gain after grafting results in the production of a high number of oxirane groups for ligand coupling. Further, these ligand groups may be spaced apart with a "spacer arm" is necessary. An excellent flow characteristic—the high degree of control provided with regard to structure and porosity—results in excellent flow-through properties. Additionally, this matrix may be completely dried between uses, thereby enhancing its flow characteristics.

The cellulose-GMA affinity matrix may be chemically modified as set out in Table I below. The purpose of this chemical modification is to prepare the matrix or preligand structure for coupling with the ligand.

TABLE I

| Basic Affinity Matrix | Method of Conversion | Functional Groups* in Converted Matrix |
|---|---|---|
| | 1. Oxidation | ⌇w⌇CH—CHO<br>　　　│<br>　　　OH |
| | 2. Amination | ⌇w⌇CH—CH₂—NHC₂H₄—NH₂<br>　　　│<br>　　　OH |
| A. Cellulose GMA matrix<br><br>⌇w⌇CH——CH₂<br>　　　　＼ ／<br>　　　　　O | 3. Thiol formation | ⌇w⌇CH—CH₂—SH<br>　　　│<br>　　　OH |
| | 4. Chelate formation | ⌇w⌇CH—CH₂—N⟨CH₂COOH / CH₂COOH⟩<br>　　　│<br>　　　OH |
| | 5. p-Benzo-quinone coupling | ⌇w⌇CH—CH₂—S—(benzoquinone)<br>　　　│<br>　　　OH |
| | 6. Dye ligand (cibcron blue) | NH—Dye |

*In this table and the following structures, ⌇w⌇ represents the substrate such as cellulose and the covalently attached moiety.

Suitable oxidizing agents for (1) above of Table I include perchlorate, sulfur trioxide, and periodate, with periodate preferred.

Suitable aminating agents under (2) above of Table I include compounds having the structural formula NH₂—R—NH₂ wherein R is a direct bond or (CH₂)$_n$.

Thiolation may be effected by using compounds such as NaSH or KSH. Table II below briefly summarizes oxidation, amination, and thiolation reactions.

TABLE II

| | Perchlorate Oxidation | ⌇w⌇CH—CH₂ ⟶ CHO<br>　　　│　│<br>　　　OH OH |
|---|---|---|
| ⌇w⌇CH——CH₂<br>　　　＼ ／<br>　　　　O | Sulfur Trioxide Oxidation | ⌇w⌇CH—CH₂SO₃⁻<br>　　　│<br>　　　OH |
| | Amination | ⌇w⌇CH—CH₂NH(CH₂)$_n$NH₂<br>　　　│<br>　　　OH |
| | Thiolation | ⌇w⌇CH—CH₂—SH<br>　　　│<br>　　　OH |

The aldehyde reaction product resulting from periodate oxidation as demonstrated at Table II above may be further treated to form a boronate affinity adsorbent according to the following equation:

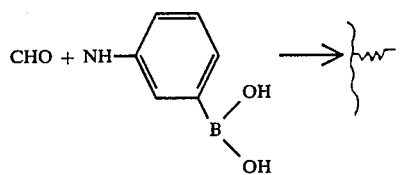

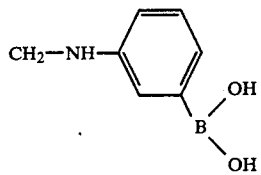

Amination with a diamine such as hydrazide proceeds according to the following equation, resulting in the formation of a hydrazide.

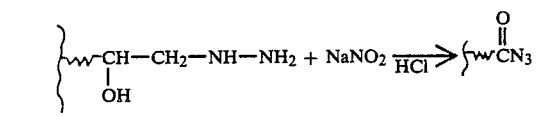

The hydrazide may be converted to the azide form according to the following equation:

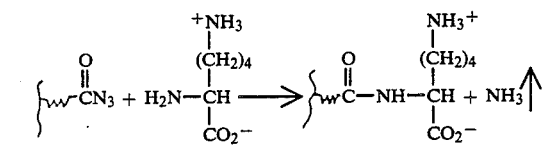

The azide may be converted to an appropriate affinity matrix by reaction with an appropriate ligand, for example, benzamidine, in accordance with the following equations:

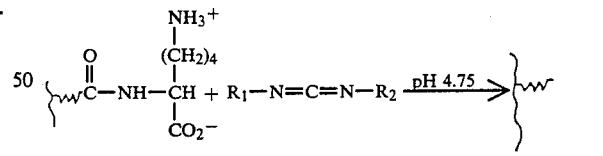

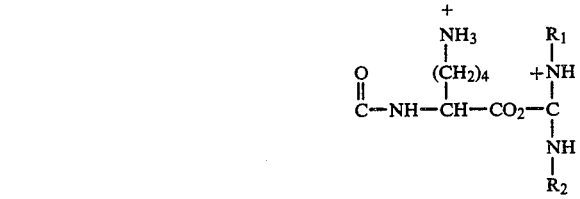

where R₁ and R₂ are C₁–C₄ alkyl.

As shown in Tables I and II above, the GMA-cellulose matrix may be thiolated with NaSH. The thiol group may then be subsequently activated by reaction with 2,2′-dipyrridine disulfide according to the following equation:

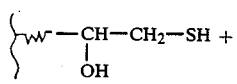

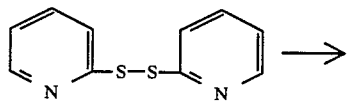

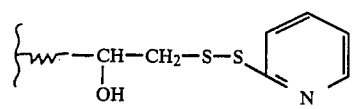

This gel will react with sterically accesible-SH groups of protein according to the following equation:

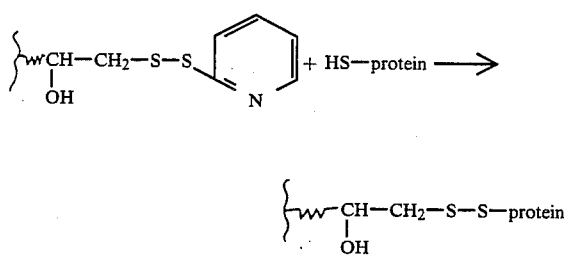

In like manner, substrates may be modified to provide an amide functional group, the amide functional group further reacted with a diamine according to the formula:

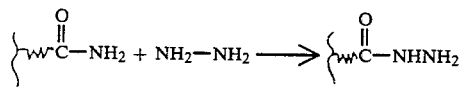

The resulting hydrazide may be subsequently treated as with the above amination of the oxirane ring.

Synthetic polymer-modified substrate with reactive hydroxyl groups may be produced utilizing compounds such as hydroxyl ethylmethacrylate (HEMA) or hydroxyl propylmethacrylate (HPMA) onto an appropriate substrate such as cellulose. Adjacent hydroxyl groups may be activated utilizing CNBr according to the following equation:

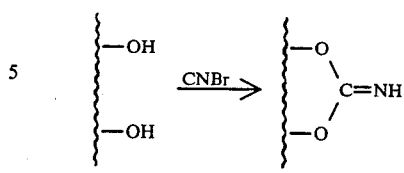

b. The Ligand And Its Coupling

The starting point for designing an affinity matrix for removal of specific enzymes is to examine the structure of the enzyme and, particularly, the structure of the inhibitors of the enzymes. The complex formation between an enzyme and its inhibitor provides the best picture of how the enzyme may be interacted with the specific protein structure. Enzyme inhibition is always competitive and reversible as expressed by the following equation:

E(enzyme)+I(inhibitor)=EI complex

Normally, the reactive site residue of the inhibitor fits into the pocket of the enzyme. In the case of kallikrein and trypsin, it is the lysine or arginine residue which interacts with the nucleophilic hydroxyl groups of kallikrein's serine active sites. In many cases, an animal enzyme inhibitor may be extracted from plants. An effective affinity matrix may thus be made by binding the plant inhibitors for enzyme adsorption. It is known that plasma kallikrein inhibitors have been isolated from potatoes and peanuts.

The resulting substrate product may be further reacted with the amine functionality of a protein to provide an appropriate affinity adsorbent according to the following equation:

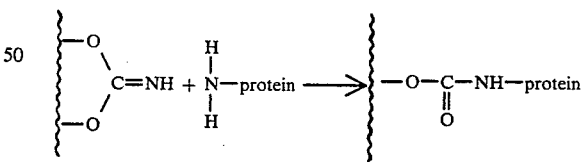

It is now known that for the coupling of an antibody or enzyme inhibitor to a solid matrix to have maximum affinity for the antigen or the enzyme it is important that the ligand retain its active conformation after coupling to the matrix.

Additionally, by utilizing the glycidyl group as a precursor, it is possible to couple another moiety through the glycidyl group. The newly linked moiety may be activated with a different activation mechanism for protein coupling as shown below in Table III.

TABLE III

| Original Functional Group | New Moiety Converted | Protein Binding Mechanism |
|---|---|---|
| ⎰∿CH—CH₂⎱ with epoxide O | Sugar (either in mono, di or trisaccharide form) | All the Sephadex^R or Sepharose^R coupling method can be applied with more flexibility |
| | Chelating | Through metallic ions |
| | Lectin (such as Con A) | Those carbohydrate binding plant seeds have specific affinity for glycoproteins |
| | Polylysine, polyarginin or other poly amino acids | Proteolytic enzyme binding |
| | Protein A | IgG binding on Fc region |
| | Polyphenol | Discussed below |

Coupling Through Polyphenol

Proteins are highly reactive toward polyphenols. The basic reaction is the addition of any nucleophilic residue on the proteins to the quinone form of the polyphenol through the following route:

Method 1

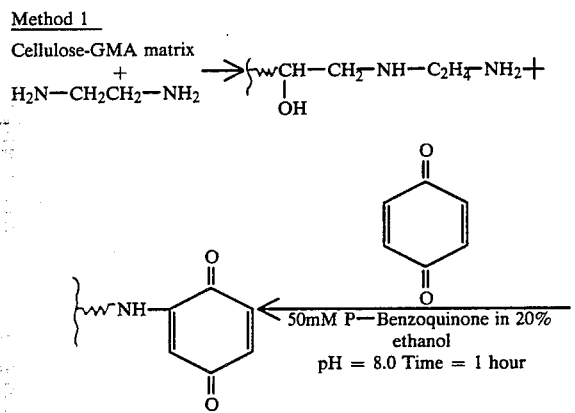

Method 2

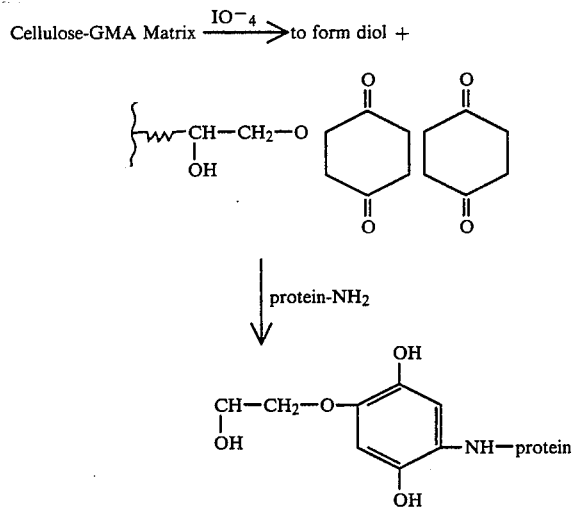

It is now known that for the coupling of an antibody or enzyme inhibitor to a solid matrix to have maximum affinity for the antigen or the enzyme it is important that the ligand retain its active conformation after coupling to the matrix. Antibody molecules exist in their active forms only in a small number of conformations and the functional affinities vary widely upon coupling to a solid surface. Thus, the noncovalent interactions between the matrix and ligand with forces such as hydrogen bonding and hydrophobic interactions have manifest influence on antibody conformations. Since antibodies are bulky in structure, the physical character of the matrix, such as surface area and pore distribution, also is a consideration from a steric hindrance point of view. For example, it has been found that above the level of about 3–4 mg/gm of IgG bound to Sepharose ®, additional bound IgG is ineffective as a ligand. Apparently, as higher levels of IgG are coupled to the Sepharose ®, antibody activity actually diminishes due to crowding of IgG, preventing the action of the antibody. Using cellulose as a substrate, maximum activity is attained at a higher level of substitution, 7 mgs. of IgG per gram of cellulose. However, by increasing the distance between the substrate and the active binding site, for example by the use of a "spacer arm," additional binding capacity is possible. Accordingly, increased antibody activity is possible by the introduction of a hydrophilic spacer arm according to the following reactions:

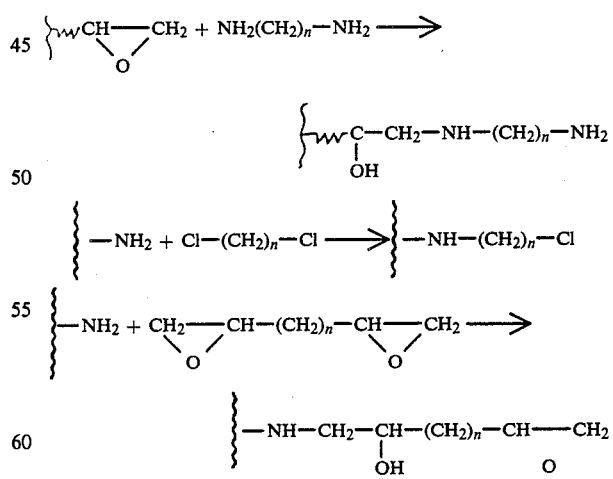

As mentioned above, the synthetic polymer-modified substrates of the present invention may be carefully tailored to particular needs by crosslinking the synthetic polymer and/or substrate. Crosslinking may be provided either by incorporating into the polymerization recipe a small amount of polyunsaturated comonomer having at least two polymerizable alpha,beta-carbon double bonds, such as for example mono- and polyethylene glycol dimethacrylates and diacrylates (with the polyethylene glycol residue containing up to six ethylene groups), ethylene dimethacrylate, ethylene diacrylate, tetramethalene dimethacrylate, tetraethylene diacrylate, divinylbenzene, triallyl cyanurate, methylene-bis-acrylamide or -bis-methacrylamide, and the like.

Another type of crosslinking agent utilizes the presence of a free pair of electrons on the aminoalkyl nitrogen atoms, where present. In this case, crosslinking may be carried out with such bifunctional reagents as would react with nitrogen free electron pairs. Among these are the diacyl halides such as $Hal-CO-(CH_2)_n-CO-Hal$, or the alkyl dihalides, such as $Hal-(CH_2)n-Hal$, wherein Hal is a halide such as chloride, bromide or iodide, and n may be anywhere between 2 and 12. Analogues of these compounds wherein $-(CH_2)_n-$ is replaced with phenyl are contemplated as well.

Figure 8:
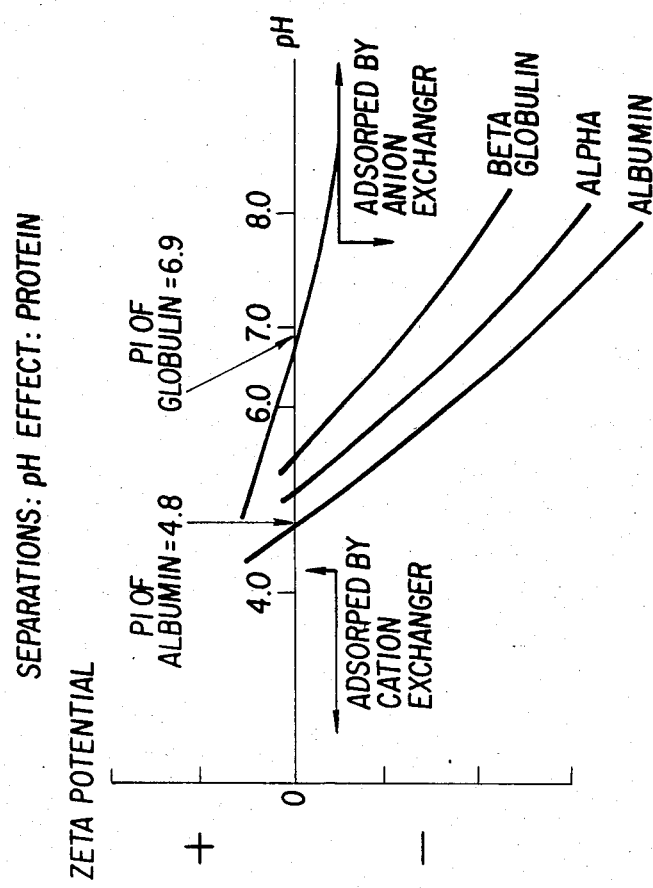
FIG. 8 is a graph comparing the isoelectric points of various human plasma proteins.

The amount of crosslinking agent is best determined empirically. It is to be considered sufficient when the polymer has achieved the desired structural integrity and porosity. Ideally, an amount of crosslinking agent between 5-20 mole percent of the synthetic polymer units is sufficient. FIG. 8 demonstrates the unique feature of a crosslinked HEMA cellulose chromatographic matrix according to the present invention. Typical ligands include DNA blood type antigen, anti-alpha feto protein, $C_1Q$, protein A, polylysine, methylated albumin, tryptophan, phenylalanine, concavaline A, and the like. For removal of proteolytic enzymes from IgG, epsilon-aminoacrylic acid, lysine, methyl-p-aminocyclohexane carboxylic acid, and trasylol, potential inhibitors, are most effective. For removal of kallikrein and PKA, benzamidine is effective.

The affinity matrices of the present invention involve the coupling of a ligand to the substrate-synthetic polymer matrix. Typically, any ligand which may be immobilized in the stationary phase and used to purify serum by the binding of a complementary molecule from a solute phase by affinity chromatography is contemplated.

D. Enzyme Removal Using Affinity Matrix As Above

1. Removal of Plasminogen Properties of The Enzyme

The blood coagulation metabolism existing in the human body occurs with two opposing processes, a fibrin-forming one associated with the blood coagulation system, and a fibrin-removing process directed by the fibrinolysin system. In normal physiological conditions, the two systems remain practically inactive. However, in the emergency state, a considerable amount of plasmin is suddenly activated from inactive precursors by intrinsic blood factors and the system is unbalanced. Clinical study has shown that the blood of individuals who have died suddenly under stresses might be in liquid and incoagulable form. This condition is now known to be due to proteolytic dissolution of fibrin by plasmin which has been activated from plasminogen. Therefore, plasminogen must be removed from IgG to eliminate the fibrinolytic effect and to avoid fragmentation of IgG.

Both plasminogen and plasmin behave as if they were gamma globulin. The isoelectric point of plasminogen has been estimated to be pH 5.6. It is probably a glycoprotein and contains small amounts of phosphorus. The molecular weight has been reported to be 143,000 or 84,000 by different investigators. The molecule behaves as if it were assymmetric in shape with an axial ratio of 9 to 16. The chemical properties of human plasmin are similar to those of plasminogen, but the molecular weight is slightly smaller due to splitting off of some molecules during activation. The conversion of plasminogen to plasmin involves change of shape from assymmetrical to more compact spherical type.

The removal of proteolytical enzymes from IgG is effected by passing the solution through an affinity matrix bonded with an enzyme inhibitor. Among all the potential inhibitors of the plasminogen system, the following three were found to be most effective:

(1) Epsilon-aminocaproic acid or lysine,
(2) Methyl-p-aminocyclohexane carboxylic acid,
(3) Trasylol.

In a preferred embodiment, the inhibitor, i.e. epislon-aminocaproic acid, is bound to a cellulose-GMA matrix, utilizing a CNBr activation. Further, since certain quaternary amines were found to exhibit plasmin activity and with plasminogen having isoelectric point 5.6, plasminogen removal by QAE and DEAEMA matrix occurs to a certain extent.

Methods of Measuring Plasminogen Activities

Caseinolytic method: Techniques developed to measure the concentration of plasminogen in human plasma depend on the proteolytic activity of plasmin. Plasminogen cannot be directly determined, but must be converted into plasmin through activation with urokinase and subsequently determining the plasmin formed from its proteolytic activity with certain substrates. Although the physiological substrate for plasmin is fibrinogen, synthetic substrate such as casein is preferred for better sensitivity and reproducibility. The principle of the caseinolytic method is to analyze the ability of the plasminogen in plasma to digest casein in a given time and be expressed as plasminogen activity. Such activity can be measured by the amount of tyrosine, equivalent released from hydrolytic dissolution of casein due to the proteolytic effect of plasmin. A standard procedure was established by NHI (National Heart Institute) Committee on Thrombolytic Agents.

2. Affinity Matrix For Kallikrein Removal

IgG made by the Cohn cold ethanol fractionation method is known to contain undesirable, deleterious exogenous activity such as prekallikrein activator (PKA) activity, activated clotting factor, and esterase activity. Those exogenous activities have been reported on intravenous administration to cause hypotensive reaction in patients, Alving et al., *New England J. Med.* 299:66 (1978). By binding the enzymatic inhibitor as ligand on, for example, a cellulose substrate, preferred is cellulose modified as above, proteolytic enzymes such as kallikrein are eliminated from the plasma. Kallikrein, like other serine protease, is also inhibited by synthetic compounds such as p-carboethoxy phenyl epsilon guanidine caproate. Benzamidine bound to cellulose-GMA is preferred as affinity ligand for kallikrein removal.

V. Sterile Filtration Of Purified IgG

At this point, after such treatment, the filtrate is essentially free of proteins other than intact IgG, i.e. pure monomeric intravenously injectable. The final step in the purification process involves a sterile filtration. Typically, the product from the affinity step above is passed through a sterile filter, typically a microporous nylon membrane. Any of the sterile filtrations known to the art are satisfactory for this step in the process.

VI. Lyophilization And Packaging

The sterile filtered highly pure IgG may then be lyophilized and packaged in sterile containers.

An additional advantage of the present invention provides for recovery of valuable side-products such as albumin and transferin. Albumin (40 g/l) and transferin (2.95 g/l) IEP=5.9), are adsorbed in the ion exchange separation step wherein the ion exchange matrix is a GMA-DEAEMA-cellulose matrix and the pH is at 6.3. Much of the transferin will be eluted out by addition of 20–30% monophosphate to the 0.01M phosphate buffer, whereas albumin elution requires the addition of 100% of monophosphate. The transferin and albumin, thus separated, may be further purified utilizing a cation exchange chromatography. FIG. 2 represents a schematic to maximize recovery of various elements within the plasma being processed, as described above. Further, by-product recovery is described in Examples 18 and 19, below.

Impurity Removal for High Purity IgG

1. Removal of Total Lipid

Human serum or plasma contains considerable amounts of lipids. Their actual content in serum varies from one to the other with respect to certain physical and chemical parameters. All the lipids in plasma form complexes with protein. Most of the fatty acid molecules are bound to albumin, while the other lipids are combined with other proteins in complexes called lipoproteins. This combination promotes solubility of the lipids in an aqueous medium. One can always observe the increase of plasma turbidity upon storage which indicates the instability of lipid in plasma. Lipids are removed by solubilizing in ethanol combined with salt precipitation in Cohn fractionation. In the present process, lipids are removed by reducing their solubility in plasma at 5:1 to 10:1 dilution with deionized water. The turbidity reduction in diluted plasma is clearly visible and the aggregated lipid particles easily separated by filtration, using the previously described cartridges for particulate separation. Frozen plasma received from the local Red Cross was thawed and diluted with deionized water at a 10:1 ratio and then adjusted to pH 6.3 by addition of 0.5M HCl. The insoluble protein which precipitated out during the dilution were removed by filtration.

2. Determination of Total Lipids Using Phosphoric Acid-vanillin Reaction

In this method, the lipid containing plasma is heated with concentrated sulfuric acid; then vanillin and phosphoric acid are added to yield a pink color. The unsaturated components of a lipid specimen is assumed to be oxidized to ketones, the ketones then condensing with vanillin under the influence of acid catalysis. Following the assumed condensation reaction, dehydration of an aldol-type intermediate is further assumed to yield a more highly unsaturated product that absorbs visible light at wavelength 520 nm. By using olive oil as a standard, the total lipid removal from plasma in the process was measued, with the following results (Table IV):

TABLE IV

| Sample No. | Sample Nature | Total Lipid (mg/d.l.) | % Removal |
|---|---|---|---|
| 1 | Human plasma before processing | 512.0 | 0 |
| 2 | After 10:1 dilution with d.i. $H_2O$ & centrifuge | 378.0 | 27% |
| 3 | After filtering through 1st cartridge | 100.0 | 80% |
| 4 | After filtering through 2nd cartridge | 0.0 | 100% |

3. Fibrinogen Removal

Fibrinogen has molecular weight 340,000 and isoelectric point 5.5 The concentration of fibrinogen in plasma is 2–4 grams per liter with molecular volume approximately $3.9 \times 10^5 \text{ Å}^3$. In Cohn fractionation, fibrinogen is precipitated out at 8% ethanol, 0.14 ionic strength, pH 7.2 at $-3°$ C. In the present invention, fibrinogen is removed by reducing its solubility in plasma under decreasing of salt concentration by 10:1 d.i. water dilution followed by cartridge adsorption.

4. Determination of Fibrinogen

The quantitative determination of fibrinogen is performed by the Clauss method (Wichman, et al., *Biochem. Biophys. Acta* 490:363 (1977)) designed by Sigma Chemical Co. in test kit form. When plasma is diluted and then clotted with excess thrombin, the low fibrinogen concentration becomes rate limiting and inversely proportional to the clotting time yielding a linear relationship when plotted on log-log paper. A calibration curve prepared from a fibrinogen reference is used to determine the fibrinogen concentration in plasma. The procedure of the testing method is fully described in Sigma Technical Bulletin No. 880. Fibrinogen level in the range of 50 to 700 mg/dl can be detected with this procedure.

a. Adsorption of Fibrinogen in Plasma by Test Tube Method

A static test (batch test) comprising mixing the 0.01M, pH 6.3 phosphate buffer pre-equilibrated solid matrix with plasma in a test tube for 40 min. and measuring the amount of fibrinogen adsorbed by the matrix shows the following results (Table V):

TABLE V

| Sample No. | Sample of 0.1 Gram Dry Weight | Plasma Volume & Conc. | Fibrinogen Unbounded | (mg/d.l.) Bound to The Matrix | % Removed |
|---|---|---|---|---|---|
| 1 | DEAEMA-GMA-Cellulose Matrix | 5 ml (conc. of 5%) | 110 | 55 | 33 |
| 2 | Wood Pulp Cellulose | | 144 | 21 | 13 |
| 3 | Commercial DEAE Cellulose | | 138 | 27 | 16 |
| 4 | Control | | 165 | 0 | 0 | b. Fibrinogen Removal by DEAEMA-GMA-Cellulose Cartridge (Continuous)

The 220 ml (25 gram material) size DEAEMA-GMA cartridge is pre-equilibrated with 0.01M pH 6.3 phosphate buffer. 50 ml of 5% human source plasma are applied to the cartridge at 1.0 ml/min. flow and collected at 10 ml aliquot for fibrinogen determination (Table VI). No fibrinogen was detectable following ion-exchange chromatography using the DEAEMA-GMA-cellulose cartridge.

3. IgA and IgM Removal

IgA (mol. wt. 160,000, 150 mg/dl in plasma) amounts in Cohn gamma globulins have been analyzed to be within a wide range of 0.07% to 8.5%. Concentration of IgM (mol. wt. 950,000 120 mg/dl in plasma) in Cohn gamma globulin similarly varies between 0.16% to 2.5%.

According to Wadsworth & Hanson, *Scand. J. Immunol.* 5:15–22 (1976), IgA should not be present in any IgG preparations for clinical use due to anaphylactic reactions caused in IgA deficient patients.

Determination of IgA and IgM by Radial Immunodiffusion

A radial immunodiffusion test kit from the Miles Laboratories was used for quantitative determination of immunoglobulin. Radial immunodiffusion involves diffusion of antigen (for example, IgA and IgM in this case) through a semisolid gel medium containing its specific antibody, resulting in the formation of a circular zone of precipitation. The diameter of this zone is a function of the concentration of the diffusing antigen.

The diffusion plate has six wells. The first three wells are used for reference sera of different concentrations and the remaining wells can be used for test specimens. Following the Accra Assay process from Miles Laboratories, Elkhart, Ind., the quantitative detection of globulin components is as follows in Table VII. International units (IU/mL) and mass units (mg/dL) for reference immunoglobulins, as recommended by the World Health Organization (WHO) have been determined by quantitation against the WHO international reference preparation 67/86. Wells 4–6 showed no IgA or IgM in detectable quantities.

TABLE VI

| Cartridge Identification | Plasma Collected | Concentration of Protein | Fibrinogen (mg/dl) |
|---|---|---|---|
| DEAEMA-GMA (25 g) | Control | 5% | 165 |
|  | 1st 10 ml filtrant | — | — |
|  | 2nd 10 ml | — | — |
|  | 3rd 10 ml | — | — |
|  | 4th 10 ml | — | — |
|  | 5th 10 ml | — | — |

The amount of IgA and IgM in the serum of the present invention are below the detectable level of the radial immunodiffusion method. It was found that both IgA and IgM were bound to the anion exchange cartridge and can be eluted separately under different elution conditions shown in the following Table VIII:

TABLE VIII

| Ion Exchange Condition | Elution Condition | Peak Ident. | IgG | IgA | IgM | Transferrin | Albumin |
|---|---|---|---|---|---|---|---|
| 8 ml human plasma applied on 1.8 gram QAE matrix at 2 ml/min. 5 psi | I = 0.01 M pH = 6.3 | $A_1$ | 36 mg | 0 | 0 | 0 | 0 |
|  | I = 0.02 M pH = 6.1 | $B_1$ | 3.1 mg | 0 | 1.02 | 20 | 0 |
|  | I = 0.025 M pH = 5.9 | $B_2$ | 0.3 mg | 0.066 | 0.25 | 2.8 | 18.0 |
|  | I = 0.05 M pH = 5.2 | $B_3$ | 0 | 2.3 | 0 | 0.7 | 335.0 |

The QAE matrix is prepared in accordance with Example 2 of this application and is the quaternized DEAEMA-GMA-cellulose matrix.

4. Polymeric Gamma Globulin Removal

Figure 9:
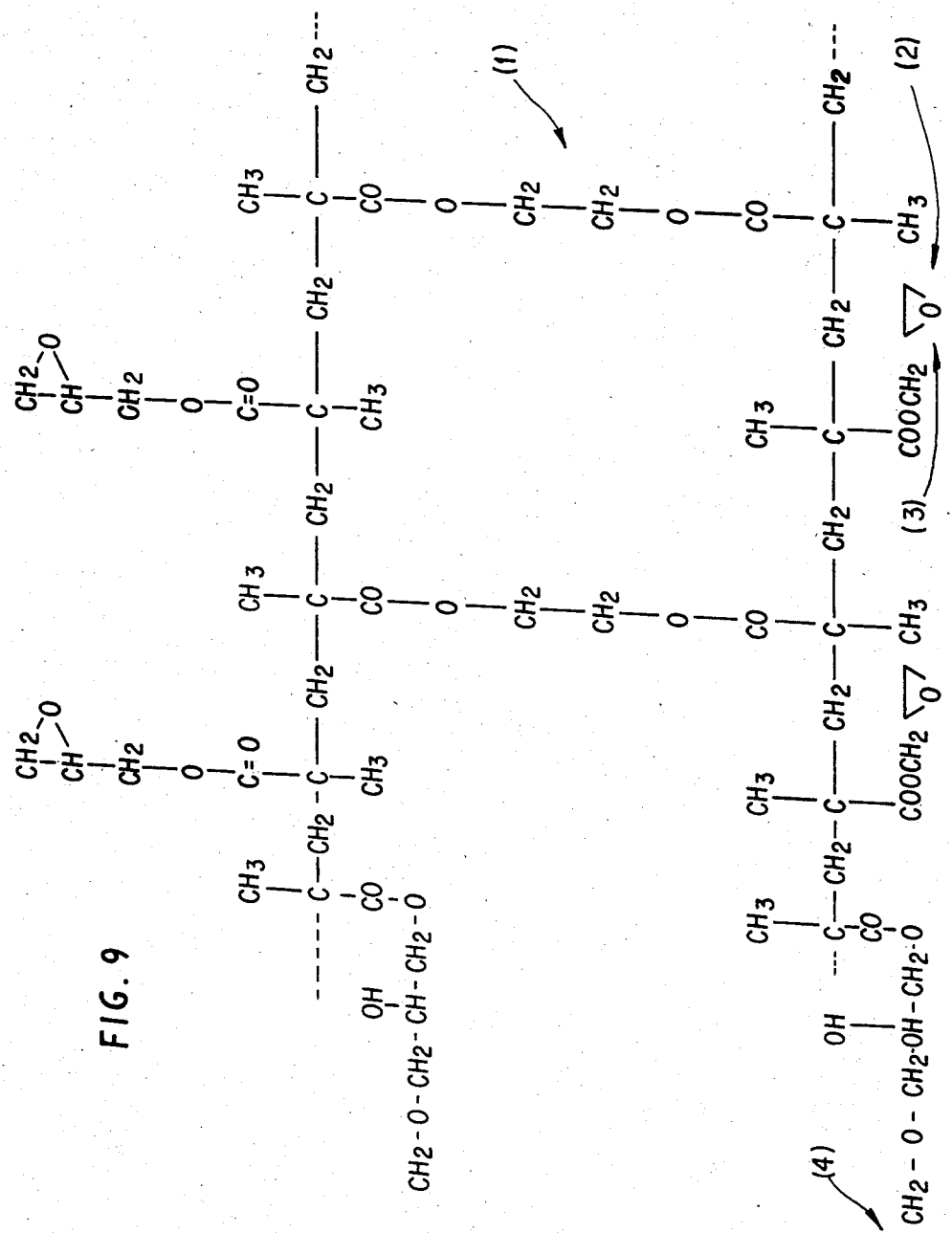
FIG. 9 is a representational drawing of a cellulose-glycidyl methacrylate matrix crosslinked with a diacrylate compound used as an affinity media in this invention.
Figure 10:
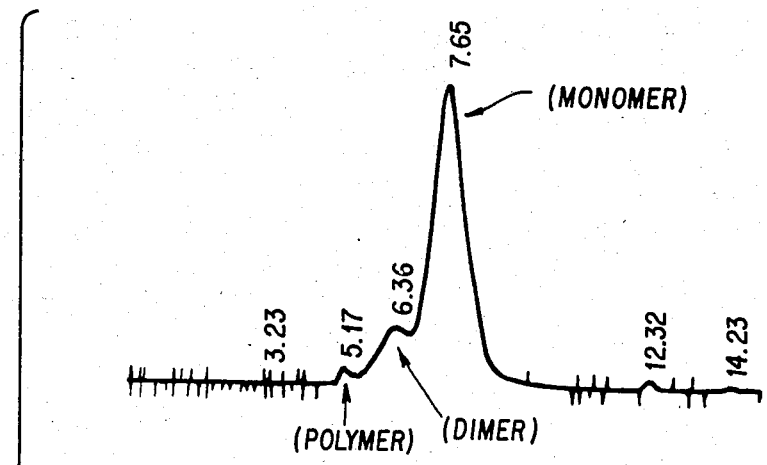
FIG. 10 is the High Pressure Liquid Chromatography (HPLC) pattern of prior art intravenous IgG (IVIgG).
Figure 11:
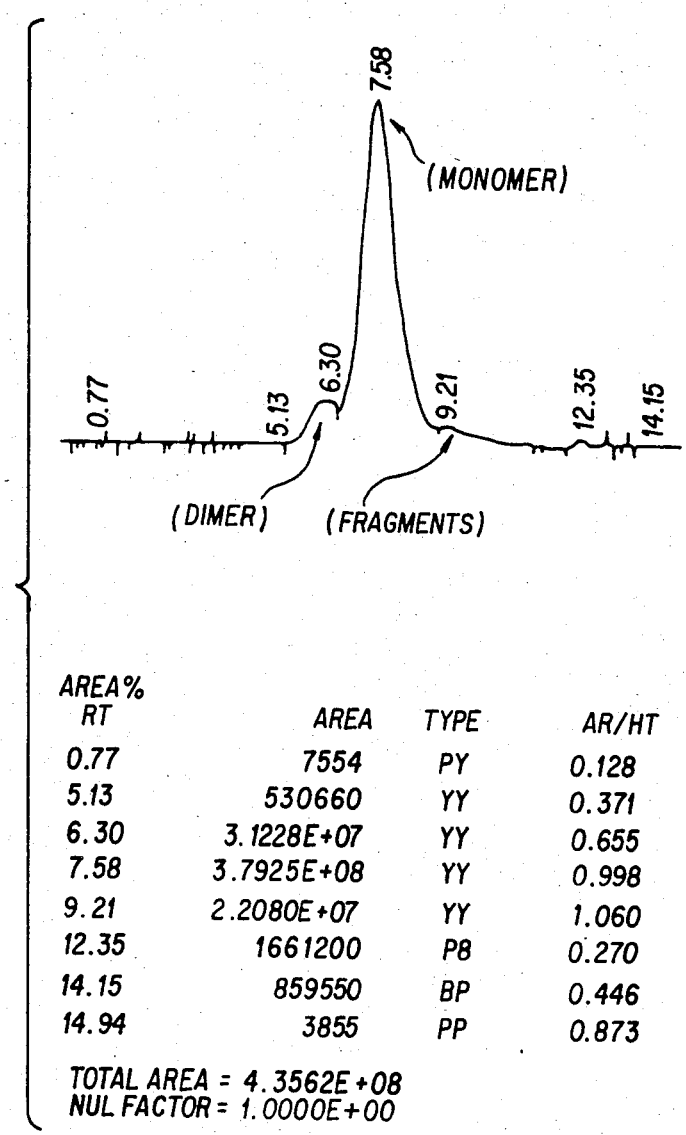

In the commercial IgG preparation by the Cohn method, a mean amount of aggregated IgG has been estimated to be 20%. The aggregates include dimers and polymers and are regarded to be the cause of the anticomplementary action which precludes intravenous use. Even the commercialized intravenous globulins still contain certain amounts of polymeric and dimeric IgG in reduced quantity. High pressure liquid chromatography was applied to identify the presence of dimers and polymers in the monomeric IgG. A spherogel TSK 3000 column by Toyo Soda with column size 7.5 mm × 30 cm is used. The mobile phase is 0.2M phosphate buffer added with 0.15M NaCl at pH 7.2, and flow at 0.5 ml/min. under 120 psi pressure. The HPLC separation pattern from the commercial lots of Immuno A.G. ® (Vienna, Austria) and Sandoz ® (Bern, Switzerland) as well as the product of this invention are shown in FIGS. 9 to 11. The product of this invention proved to be a superior preparation due to the absence of both dimeric and polymeric IgG forms.

In order to further demonstrate the efficiency of removing dimeric and polymeric IgG by the ion exchange cartridge of this invention, the IgG polymers may be generated by heating monomeric IgG (10 mg/ml) in a water bath at 62±0.1° C. for different periods of time; each preparation then cooled in an ice bath.

Figure 12:
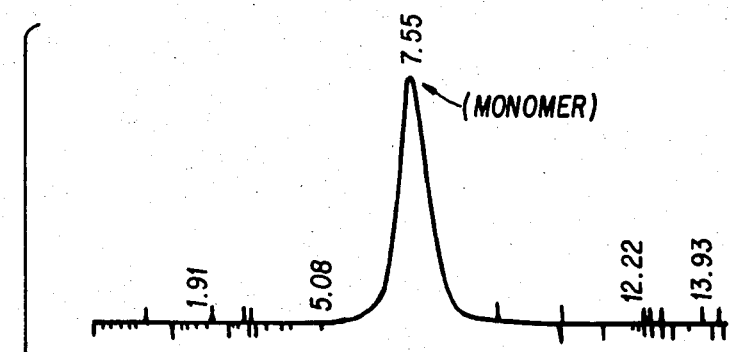
FIG. 12 is the HPLC pattern of IVIgG prepared in accordance with the present invention.

The polymeric IgG, thus prepared, shows an identifiable small peak following the monomer. The peak size increases with increasing heating time but can be completely removed by passing the heat-treated IgG through the cartridge as shown in FIG. 12.

5. Proteolytic Enzyme Removal

The use of IgG preparation made by Cohn fractionation has been associated with vasoactive reactions that range from pain at the injection site to flushing, anxiety, and even hypotension. Similar reactions to plasma protein fraction (PPF) equivalent to fraction IV-4 plus V have been associated with the vasoactive enzyme prekallikrein activator (PKA). The combination of ion exchanger and affinity cartridge proved to be an effective means of removing contaminants with vasoactive properties from any plasma products such as intramuscular IgG and PPF.

Test Results

The Bio-Rad protease detection kit was used for determining the possible existence of plasminogen in IgG. The kit consists of a casein substrate gel tablet, one vial of urokinase, and two vials of 5 ml each of a positive control serum containing serum plasminogen. To activate plasminogen, 15 μl of urokinase is reacted with 15 μl of IgG sample and incubated for 60 min. at 25° C. 25 μl of the urokinase-treated sample was applied to a protease detection gel tablet in a 2 mm diameter punched hole. The plate was incubated for 16 hours to let the plasminogen digest casein which is imbedded in the gel. Termination of the protease digestion and enhancement of the ring was accomplished by overlaying the plate with a solution of 3% acetic acid. The diameter of the rings measured directly the amount of plasminogen in the sample. The IgG of this invention has no detectable amount of plasminogen as the ring formation is not shown in the gel structure.

The PKA activity was compared to that of FDA Ref. 1 or 2. Ref. 1 is a lot of plasma fraction that was associated with hypotensive reaction and contains PKA at a concentration of 45 ng/ml. Kallikrein activity was expressed that will hydrolyze 0.1 mM S-2302 (Helena Laboratories, Beaumont, Tex.) at an initial rate of 1 μmol/min. at pH=8.0 and 22±1° C.

The results are shown at Table IX.

6. Hepatitis (HBsAg) Test

HBsAg determinations were performed by Ausria II-125 test kit of Abbott Laboratories, a solid phase radioimmunoassay technique to measure HBsAg levels in serum. Polystyrene beads coated with guinea pig antibody are supplied in the kit. 500 μl of gamma globulin is added and, during incubation, HBsAg, if present is fixed to the antibody. When antibody tagged with $^{125}I$ is added, it binds to any HBsAg on the beads creating an antibody-antigen-antibody sandwich. Within its detectable range, which is limited by the number of antibodies capable of binding on the polystyrene bead surface, the greater the amount of antigen in the testing specimen, the higher the final count. Based upon the Abbott's result, the sensitivity of Ausria II-125 is around 0.1 μg/ml. No HBsAg can be detected by the Ausria solid phase RIA kit in both gamma venin and zeta globulin as shown in Table X, two preparations of this invention.

TABLE IX

| Sample No. | Plasma Sample | PKA % to Ref. 2 | Kallikrein mu/ml |
|---|---|---|---|
| 1 | Whole plasma before processing | 50% | 200 |
| 2 | DEAE treated plasma | 10% | 2,000 |
| 3 | Sample 2 further processed by affinity cartridge | 8% | 20 |

TABLE X

| Specimen Identification | Counts per Min. Reading from Gamma Counter |
|---|---|
| Negative control | 134.00 |
| Positive control | 7,009.00 |
| Zeta globulin (50 mg/mL) | |
| sample 1 | 140.00 |
| sample 2 | 120.00 |

TABLE X-continued

| Specimen Identification | Counts per Min. Reading from Gamma Counter |
|---|---|
| Gamma venin (50 mg/mL) | |
| sample 1 | 140.00 |
| sample 2 | 130.00 |

According to the specification of the test kit, the presence or absence of HBsAg is determined by relating net counts per minute of the unknown sample to net counts per minute of the negative control mean times the factor 2.1. Unknown samples whose net count rate is higher than the mean cut off value established with the negative control are to be considered reactive for HBsAg. The products of this invention are negative to the HBsAg test.

7. Removal of Other Protein Species by the Ion Exchange Cartridge

About 90% of the plasma proteins are negatively charged and consequently bound to the ion exchanger under the condition of 0.01M PB at pH 6.3. The instability of enzymes in plasma occurs when their inhibitors are inadvertently removed by the cartridge. The enzyme inhibitors of Table XI below are very likely adsorbed in DEAEMA-GMA cartridge due to their negative character.

TABLE XI

| Molecule | Plasma Concentration | Structure | IEP | Inhibits |
|---|---|---|---|---|
| $\alpha_2$-macroglobulin ($\alpha_2M$) | 0.4–4 mg/ml | Mol wt 700,000 four chain polymeric protein | 5.2 | Plasmin Plasma plasminogen activator |
| C1 inhibitor (C1 in) | 0.18 mg/ml | Mol wt 105,000 single chain | 2.8 | Kallikrein XIIa Kallikrein Plasmin |
| Anti-thrombin III (AT-III) | .30 mg/ml | Mol wt 62,000 single chain | 4.0 | Plasmin |
| $\alpha_1$-anti-trypsin ($\alpha_1$-AT) | 1.5-3 mg/ml | Mol wt 50,000 | 4.0 | Plasmin |

8. Pyrogen Removal

Bacterial lipopolysaccharides (LPS) are recognized as the major cause of pyrogenic reactions from parenteral solutions. The endotoxin from gram negative bacteria resides in the lipopolysaccharide (LPS), which, with phospholipid and protein, makes up the bulk of the outer cell membrane. The LPS is an amphiphile carrying negative charge which can be removed by the positively charged ion exchange matrix. Endotoxin will interact with complements in plasma and induce intravascular coagulation if not removed. The pyrogen test is performed by using the limulus amebocyte lysate (LAL) test purchased from Associates of Cape Cod, Woods Hole, Mass. The endotoxin activates an enzyme in LAL which then reacts with a low molecular weight clottable protein to form a gel. The pyrogen test for IgG of this invention shows negative on the highly sensitive 3 picogram per ml endotoxin stamdard.

Product Control Test

Table XII following shows the major control test performed on our intravenous IgG production.

TABLE XII

| Determination | Condition | Results Lot #12 | Lot #12 & HSA |
|---|---|---|---|
| 1. IgG content | >90% of total protein | 98% | 96.8% |
| | >50 mg/ml | 43.7 mg/ml | 40.3 mg/ml |
| | 90–100% of indicated content | 87.4% | 80.5% |
| 2. Aggregated IgG | negative | negative | negative |
| 3. Immunological Test | human specific IgG specific | human specific IgG specific | human specific IgG specific |
| 4. Anti-complement Activity | <20 unit/ml | 18.4 unit/ml | 7.5 unit/ml |
| 5. Anti-Diptheria Toxoid | >2 unit/150 mg IgG | 8.1 unit per 150 mg IgG | 8.1 unit per 150 mg |
| 6. Anti-measles | >5 unit/150 mg IgG | 5.4 unit/150 mg IgG | 15.3 unit/150 mg IgG |

In addition to the above control test, the product should be subjected to and pass the following test:
1. Protein content by modified Microkjeldal termination of nitrogen.
2. Moisture content <3%.
3. IgG purity by HPLC and Electrophoresis.
4. IgG content and Isotonicity. Zetaglobulin dissolved in D.I. water at a concentration of 50 mg/ml was not isotonic, it should be dissolved in 0.01M phosphate buffer—0.05M NaCl pH 7.0.
5. IgA and IgM test by radio immunodiffusion.
6. Stability Test. When 2 ml of the test material is heated in a 12×75 mm stoppered glass tube at 57° C. for 4 hours, it shall not show any visible sign of gelation.
7. Sterility test.
8. Pyrogen test.
9. ACA test for IgG The test for freedom from anti-complementary effect is based on the reaction between the test sample and complement of guinea-pig.

Test Procedure

To 1 ml of test material, 100 units of guinea-pig complement contained in 1 ml of any appropriate buffer solution and 3 ml of same buffer solution shall be added.
a. The residual complement units in the mixture incubated at 37° C. for 1 hr.
b. The residual complement units in the blank mixture (without the test sample).
 i. The value of (b) shall be more than 85 units.
 ii. The inactivated complement units (AC) is calculated by the following formula: $AC = b - a$

Criterion for Judgment

No more than 20 units of complement shall have been inactivated.

Having now generally described this invention, the same will be better understood by reference to certain specific examples which are included herein for purposes of illustration only, and are not intended to be otherwise limiting.

EXAMPLE 1

DEAEMA-GMA-Cellulose Ion Exchange Matrix (a) Formulation

| Reagent | Quantity |
|---|---|
| Microcrystalline cellulose | 10.0 g |
| Diethylaminoethyl methacrylate | 25.0 cc |
| Glycidyl methacrylate | 2.5 cc |
| Ammonium persulfate | 1.0 g |
| Sodium thiosulfate | 1.0 g |
| Water | 500.0 cc |

(b) Procedure
1. Cellulose was well dispersed in water in a reactor.
2. Diethylaminoethyl methacrylate and glycidyl methacrylate were well mixed before pouring into the reactor.
3. After pouring the monomers into the reactor, the mixture was stirred for 5 minutes.
4. Ammonium persulfate and sodium thiosulfate were dissolved in 20 ml water and then poured into the reactor.
5. The reactants were stirred for 20 minutes at 15° C. to 40° C.; the temperature was then increased to 80° C.
6. Stirring was maintained for 1 hour in the range of 80°–90° C.
7. A period of 0.5 hour was allowed to cool down the products.
8. The product was filtered and washed well with water and acetone.

(c) Results

The number of available DEAEMA functional groups was determined by titrating the 0.1M $HClO_4$ in glacial acetic acid (0.1M HCl in aqueous solution) on a Brinkman Potentiograph E 536. The instrument was calibrated by measuring commercial DEAE cellulose as the control, and capacity was expressed as milliequivalent (meq) gram of dry material. The copolymerized cellulose showed approximately three times more capacity than that of the cellulose made from the conventional prior art derivative method.

The results were further confirmed by the measurement of albumin adsorption capacity using the beaker test method for determining adsorption capacity. This was done by slurrying one gram of media in 50 ml of 0.01M PB at pH 6.3 and then adding albumin at a concentration of 5% protein, followed by room temperature agitation for one hour. Supernatant was evaluated for protein content using a UV spectrophotometer at O.D. 280 nm to evaluate adsorbed protein by difference. The capacity is expressed in milligrams per gram of matrix. The amount of albumin measured at 280 nm O.D. showed the following results (Table XIII):

TABLE XIII

Beaker Test on DEAEMA-GMA-Cellulose

| Sample No. | Sample Weight (Dry/Wet) | pH Media in Buffer | 0.1 M NaOH Added | Media in BSA | BSA Conc. | Capacity Test A280 t = 1 hr | (Mg/g) |
|---|---|---|---|---|---|---|---|
| 1 | 1/9.9 | 5.63 | 2.7 ml | 6.25 | 1030 mg | 0.25 | 991 |
| 2 | 1/8.7 | 5.5 | 3.2 | 6.25 | 1030 | 0.33 | 978 |
| 3 | 1/8.33 | 5.68 | 2.8 | 6.25 | 1025 | 0.38 | 966 |
| 4 | 1/7.69 | 5.68 | 2.8 | 6.25 | 1025 | 0.69 | 918 |
| 5 | 1/7.69 | 5.68 | 2.8 | 6.25 | 1895 | 4.5 | 1195 |
| 6 | 1/8.7 | 5.57 | 3.9 | 6.30 | 1025 | 0.19 | 995 |
| 7 | 0.88/8.0 | 5.5 | 3.6 | 6.30 | 1533 | 1.49 | 1298 |
| 8 | 1.0/8.33 | 5.52 | 3.3 | 6.25 | 1030 | 0.36 | 974 |
| 9 | 1.0/8.33 | 5.52 | 3.3 | 6.25 | 1236 | 0.97 | 1085 |

As may be seen from Table XIII, BSA bindings as high as almost 1300 mg/gram of DEAE-GMA-cellulose matrix are possible under the described conditions.

EXAMPLE 2

DEAEMA-GMA-Cellulose (a) Recipe

| Reagent | Quantity |
|---|---|
| Poly(diethylaminoethyl methacrylate)-g-cellulose (Example 1) | 5.0 g |
| 1,6-Dichlorohexane or 1,4 dichlorobutane | 3.0 cc |
| Potassium iodide | 0.1 g |
| Water | 100.0 cc |

(b) Procedure
1. A round neck flask was filled with poly(diethylaminoethyl methacrylate)-g-cellulose, 1,4 dichlorobutane, potassium iodide and water.
2. The reaction mixture was refluxed overnight.
3. The product was filtered and washed well with acetone and water.
4. The sample was acidified with $10^{-2}$N HCl, then washed well with water.

(c) Results

The results demonstrate the effectiveness of 1,6-dichlorohexane as a crosslinker on fixing the charged groups. 1,6-dibromo or diiodo hexane have also been applied as crosslinkers with success.

To improve quaternization percentage, water soluble quaternization reagents, halo compounds, such as 1,3-dichloro-2-propanol, chloroacetic acid, methyl chloroacetate and chloroethyl diethylamine can be applied with success. The quaternized (QAE) media derived from ethyl iodide showed exceptionally high BSA binding capacity in the pH range from 7 to 8.5. The results are shown in Tables XIV and XV.

TABLE XIV

Quaternization Percentage in QAE Media Derived from Different Q-Reagents

| Sample No. | Q-reagent | Q (%) |
|---|---|---|
| QAE-1 | 1-chloro-2-propanol | 13 |
| QAE-2 | 1,2-dichloro-2-propanol | 77 |
| QAE-3 | methyl chloroacetate | 83 |
| QAE-4 | chloroethyldiethylamine | 82 |
| QAE-5 | ethyl iodide | 80 |

TABLE XV

BSA Capacity of Various QAE Media vs. pH of Phosphate Buffer Solution

| Sample No. | Q-reagent | BSA Cap. (Mg/g) | pH | BSA Cap. (Mg/g) | pH | BSA Cap. (Mg/g) | pH |
|---|---|---|---|---|---|---|---|
| QAE-1 | methyl chloroacetate | 1527 | 6.29 | 1027 | 7.36 | 758 | 8.69 |
| QAE-2 | 1-chloro-2-propanol | 1376 | 6.30 | 671 | 7.30 | 336 | 8.12 |
| QAE-3 | 1,2-dichloro-2-propanol | 1466 | 6.25 | 676 | 7.29 | 387 | 8.18 |
| QAE-4 | ethyl iodide | 1391 | 6.27 | 1015 | 7.59 | 816 | 8.26 |
| QAE-5 | 1-chloro-2,3-propanediol | 1397 | 6.28 | 692 | 7.33 | 367 | 7.98 |
| QAE-6 | chloroethyl diethylamine | 1483 | 6.27 | 559 | 7.39 | 290 | 8.60 |
| DEAE | — | 1625 | 6.38 | 738 | 7.32 | 296 | 7.98 |

EXAMPLE 3

Cellulose-GA Matrix Modified With Sulfopropyl Groups For Ion-Exchange Chromatography (a) Formulation

| Reagent | Quantity |
|---|---|
| Refined Cellulose | 5.0 g |
| Ethoquad C/25 | 0.5 ml |
| Glycidyl Acrylate | 10.0 ml |
| Na$_2$SO$_3$ | 13.3 g |
| Ammonium persulfate (APS) | 0.5 g |
| Sodium thiosulfate (STS) | 0.5 g |
| 1.0 M HCl | 16.67 ml |
| D.I. (deionized) H$_2$O | 250 ml |

(b) Process
1. Cellulose was well dispersed in water in a reactor.
2. Glycidyl acrylate, APS and STS were added to the reactor, with agitation, and the temperature maintained at 80° C. for one hour, the GA grafting to the cellulose after polymerization.
3. The HCl and Na$_2$SO$_3$ were added and the temperature maintained at 80° C. for four hours with agitation.
4. The recovered modified cellulose was washed twice with 2 liters of D.I. H$_2$O and evaluated for binding capacity.

(c) Test

Using the Beaker Test described above, the modified cellulose of this Example was evaluated at various pH conditions and demonstrated the bovine gamma globulin binding capacity as set out in Table XVI below.

TABLE XVI

| pH | Adsorption Capacity (mg/g) |
|---|---|
| 3.0 | 400–600 |
| 4.0 | 650–800 |
| 5.0 | 950–1200 |

Thus, the sulfopropyl modified cellulose-GA (SP) matrix demonstrates excellent binding characteristics for IgG in the pH range of 3.0–5.0, with 5.0 being preferred.

EXAMPLE 4

Cellulose-GMA Matrix Modified With Methacrylic Acid To Produce The CM Matrix For Ion-Exchange Chromatography (a) Formulation

| Reagent | Quantity |
|---|---|
| Refined cellulose | 5.0 g |
| methacrylic acid | 12.5 ml |
| GMA | 1.25 ml |
| APS | 0.5 g |
| STS | 0.5 g |
| D.I. H$_2$O | 250 ml |

(b) Process

The grafting-polymerization technique of Example 3 above was followed. At the end of the reaction, the matrix (CM matrix) was washed five times with 1.8 liters of D.I. H$_2$O and evaluated for IgG adsorption using bovine IgG and the beaker test described above. The results are shown in Table XVII below.

TABLE XVII

| pH | Adsorption Capacity (mg/g) |
|---|---|
| 5.5 | 619 |
| 6.5 | 700 |

Thus, the CM matrix shows excellent binding capacity for IgG in the 5.5 to 6.5 pH range.

The following three examples demonstrate the procedure and condition for formation of the affinity stationary phase. Examples 5 and 6 are directed to the formation of the pre-ligand matrix; Example 7 is directed to the coupling of the benzamidine ligand.

EXAMPLE 5

Preparation of Cellulose-GA Pre-Ligand Affinity Matrix (a) Formulation

| Reagent | Quantity |
|---|---|
| Refined cellulose | 5.0 g |
| Glycidyl acrylate | 10.0 ml |
| Ethoquad C/25 | 0.5 ml |
| APS | 0.5 g |
| STS | 0.5 g |
| 1.0 M HCl | 16.67 ml |
| D.I. H$_2$O | 250 ml |

(b) Process

The cellulose was dispersed in the 250 ml of D.I. H$_2$O with agitation at 80° C. and the glycidyl acrylate added to the reactor. Temperature and agitation were maintained, the APS, STS and HCl added, and the reaction permitted to proceed for one hour. The covalently bonded celluloe-GA pre-ligandized matrix was removed, washed with 7×2 liters of deionized water and stored for further treatment (conversion to affinity ligand as in Example 7 below).

EXAMPLE 6

Preparation of Cellulose-GMA Pre-Ligand Affinity Matrix (a) Formulation

| Reagent | Quantity |
|---|---|
| Refined cellulose | 5.0 g |
| Glycidyl methacrylate | 12.5 ml |
| APS | 0.5 g |
| STS | 0.5 g |
| D.I. H$_2$O | 250 ml |

(b) Process

The cellulose was dispersed in the D.I. H$_2$O with agitation and heated to 80° C., with agitation. The glycidyl methacrylate, APS and STS were added to the reactor and the reaction permitted to proceed for one hour. The reaction was terminated and the covalently bound GMA-cellulose matrix removed, washed with 5×1.8 liters of D.I. H$_2$O and stored for further processing (conversion to affinity ligand as in Example 7 below).

EXAMPLE 7

Preparation of Affinity Matrix with Benzamidine Ligand

The GMA-cellulose matrix of Example 6 was washed with five volumes of deionized H$_2$O. The washed GMA-cellulose matrix was treated with a 1.5% aqueous solution of NaIO$_4$ at room temperature, five volumes of the NaIO$_4$ solution circulated through the matrix for 1 to 2 hours at room temperature. The resulting matrix, the epoxy groups now converted to aldehyde groups by the NaIO$_4$ solution, was washed with 10 volumes of deionized water at 25° C. and equilibrated with 0.01M phosphate buffer at pH 7.8. Benzamidine in a concentration of 20 mg/ml was circulated through the aldehyde-pendant matrix at a flow rate of 2 cc/min overnight at 4° C. in the presence of NaCNBH$_3$, concentration approximately 1 mg/ml. Alternatively, the coupling of benzamidine may be effected at room temperature by circulating the above benzamidine solution at room temperature for 8 hours. Following coupling, any uncoupled protein was removed from the matrix by washing with phosphate buffer at pH 7.8. Any remaining aldehyde groups were deactivated by circulating glycine ethylester at pH 6.5 in the presence of NaCNBH$_3$ for 4 hours, the glycine ethylester produced by dissolving 1 g of glycine ethylester hydrochloride in 100 cc of deionized water, the pH adjusted to 6.5 by addition of sodium hydroxide solution.

The following Example 8 demonstrates the ion-exchange matrix utilized in a "stacked pad" column configuration, the pads comprising a mixture of the cellulose-GMA-DEAEMA formulation of Example 1 and modified silica.

EXAMPLE 8

Formulation of a Sheet Containing Both Modified Cellulose and Modified Silica (a) Silanization of Silica The silanization process can be performed either in toluene or in water. The reaction mechanism involves condensation of the halide or silanol functional groups on the organo-silane with silanols on the silica surface. Therefore, the reaction conditions depend very much on the nature of the silane and the surface property of silica. The selection of silica is made based on both chemical and physical factors. Chemically, it should have a surface property favorable for silanization reactions; physically, the particle size should be large enough to permit the least amount of pressure build-up in a column up to 2 ft. in length as long as the composite structure homogeneity can be maintained in the formulation. The following three grades of silica gel from Davidson Chemicals are the choice to meet such requirements:

| Grade | Approx. Particle Size (Micron) | Surface Area (m$^2$/g) | Pore Vol. (cc/g) | Pore Dia. A | pH 5% Slurry |
|---|---|---|---|---|---|
| 922 | 50 | 750 | 0.43 | 22 | 4.0 |
| 950 | 30 | 600 | 0.43 | 25 | 6.0 |
| 952 | 70 | 320 | 1.50 | 250 | 7.0 |

The maximum pore diameter from Davidson's product is arond 250 A, which can only accommodate protein molecules smaller than albumin. Controlled pore glass of 1000 A or controlled pore silica of 500 A needs to be used to facilitate the diffusion of larger protein molecules such as IgG or immune complex. DEAE is introduced onto silica gel through the following route:

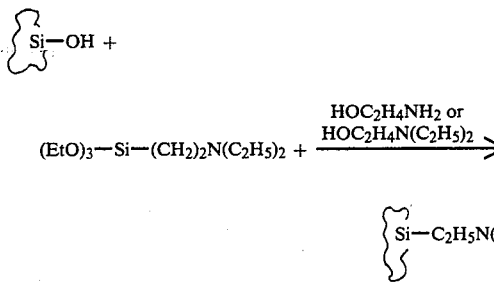

(b) Formulation of the Slurry

The modified cellulosic fiber from Example 2 and the silanized silica from (a) were mixed in a tank at 1 to 2% consistency to form a slurry according to the following formulations (Table XVIII) below.

Alternately, copolymerization can be performed on the mixture of large and small refined pulp in the same reactor. Silica 952, being large in size (70 micron or larger), can be held by the modified cellulose alone without refined pulp. No binder is required, since the polymer on cellulose is also functional as a binder.

(c) Formation of a Column

The slurry was cast onto a foranimous surface, vacuum felted, and dried in a conventional manner. The flat, dimensionally stable sheet was then cut to the appropriate diameters for each type of column. The cut discs were stacked in the cylinder in an appropriate height.

(d) Discussion and Results

The above prepared matrix was cut to 9.0 mm diameter sized discs and stacked to 6-inch length with 0.85 grams of dry weight material. After following the swelling, adsorption and elution procedures, the albumin adsorption capacity was measured and the number of DEAE groups was titrated, with the results shown in the following Table XIX below.

TABLE XVIII

| Sample No. | Modified (Long Cellulosic) Fiber (%) | Refined Pulp (+40 CSF) % | DEAE on Silica 952 % | % Retention |
|---|---|---|---|---|
| 1 | 20 | 10 | 70 | 90 |
| 2 | 30 | 0 | 70 | 80 |
| 3 | 30 | 20 | 40 | 95 |
| 4 | 50 | 0 | 50 | 90 |
| 5 | 20 | 7%(+40) & 7%(−10) | 60 | 100 |

TABLE XIX

| Exp. No. | Matrix Characterization | | | Capacity | |
|---|---|---|---|---|---|
| | Modified | +40 Refined Pulp | Silica 952 | By Titration (MEQ/G) | Albumin Adsorption (mg/g) |
| 1 | 20% (Inact.) | 10% (Inact.) | 70% (Act.) | 0.89 | 171 |
| | | | | | 182 |
| 2 | Act. | — | Act. | 2.0 | 245 |
| | | | | | 249 |
| 3 | Act. | — | Act. | 1.0 | 120 |
| | | | | | 123 |
| 4 | Inact. | Inact. | Inact. | 0 | 0 |
| 5 | 100% Act. | — | — | 2.0 | 264 |
| | | | | | 270 |

The results fully demonstrate the contribution of the ion exchange functional groups from the organic matrix. The enhanced capacity is achieved by making cellulose and binders all contributing their available sites for ion exchange, in addition to silica.

The following examples show the use of the carrier of the invention in a fibrous matrix used in column form and in cartridge configuration to separate IgG.

EXAMPLE 9

Plasma Fractionation Using the Media of Example 2

775 ml of Cohn fractions II and III from human plasma were dissolved in 0.01M phosphate buffer at pH 6.5. This solution was added to a column (7.7 cm i.d. × 4.3 cm length, vol = 200 ml) containing 25 g of the media of Example 2. 2.7 g of IgG were recovered from the non-bound fractions whereas elution of bound material with 1M sodium chloride yielded 7.5 g of albumin.

Thus, the quaternized cellulose-GMA-DEAEMA stationary phase, formed into pads and packed into a column, will bind non-IgG proteins such as albumin at the appropriate PI of IgG.

EXAMPLE 10

Separation of Protein Mixtures by DEAEMA-GMA Cartridges

In this example, it is demonstrated that DEAEMA-GMA cartridges, like columns, can be utilized to separate protein mixtures with a high degree of resolution. Unlike columns, the cartridges have no undesirable pressure problems and can therefore be operated at a high flow rate with low pressure drop. In fact, out of 15 cartridges tested, all units gave reproducible and comparable results.

Experiment A shows the separation of an artificial mixture of bovine gamma globulin and bovine albumin. Experiment B shows the fractionation of human plasma. Cartridges (diamter 2.5 cm, height 7.5 cm) were used in both of these experiments.

Experiment A

Protein: A mixture of two subclasses of gamma globulin (483 mg) and bovine serum albumin (432 mg)
Buffers:
Buffer A: Phosphate buffer (0.01M) at pH=6.8.
Buffer B: Phosphate buffer (0.05M) at pH=6.0
Buffer C: Phosphate buffer (0.05M) at pH=6.2+1M NaCl 282 mg gamma globulin Type I (100% pure) was eluted with 1M NaCl in Buffer A.

148 mg gamma globulin Type II (approximately 90% purity) was eluted in Buffer B.

Albumin (95% purity) was eluted in Buffer C.

Experiment B

Protein: 10 mL plasma, pH=6.8 (adjusted pH)
Gradient elution: 0.01M phosphate buffer (pH=6.8 to 4.5)
Peak I: gamma globulin
Peak II: Transferrin
Peak III: Albumin Electrophoretic studies indicate that the fractions are at least 90% pure.

Yield and Recovery

| Protein applied: | 10 mL plasma total O.D.$_{280}$ = | 390 |
| --- | --- | --- |
| | gammaglobulin, O.D.$_{280}$ = | 59.4 |
| | Transferrin, O.D.$_{280}$ = | 44.0 |
| | Albumin, O.D.$_{280}$ = | 163.0 |
| | Other eluted proteins = | 84.06 |
| | | 350.46 |
| | Yield = 88% | |

EXAMPLE 11

Elution of Bound Transferrin by pH Shift Using DEAEMA-GMA Cartridge

DEAEMA-GMA cartridge media reduces protein binding capacities at a more alkaline pH than 7.0. This unique pH shift has been utilized to elute bound proteins at higher pH without the use of salts and subsequent dialysis or ultrafiltration.

A previous study had shown that 85.4% bound BSA was eluted with (0.1M) phosphate at pH 7.5. In the present example, a similar observation was found with transferrin. Transferrin was bound to a DEAEMA-GMA cartridge media with a (0.01M) phosphate buffer at pH=6.8, and eluted with (0.01M) phosphate, pH=7.5. 92% bound transferrin was eluted in one column volume. The remaining transferrin was eluted with (0.1M) phosphate pH=7.5 and (1M) NaCl.

EXAMPLE 12

Use of DEAEMA-GMA Cartridge for IgG Fractionation

1. DEAEMA-GMA Cartridge

Applied Protein: Dialysed human plasma
Binding Conditions: Phosphate Buffer (0.01M: 0.9–1.2 mS) pH=6.3
Elution Conditions (continuous or step is usable):

| | [Buffer] | Conductivity | pH |
| --- | --- | --- | --- |
| IgG | 0.01 M | 1.0 mS | 6.8 |
| Transferrin | 0.025 M | 1.75 mS | 6.04 |
| Albumin | 0.06 M | 3.85 mS | 5.14 |

EXAMPLE 13

Ion Exchange Chromatography Separation of the Plasma

In this experiment, the DEAEMA-GMA cartridges of Example 10 were used. Eight of three cartridges were connected in series, the total weight of matrix in the cartridge assembly being approximately 2,400 g. The cartridges were swelled and equilibrated by passing 48 liters of 0.1 molar phosphate buffer, pH 6.75, at 500 ml/min followed with a 0.01M phosphate buffer, pH 6.4, until the conductivity and pH of the effluent were the same as those of the buffer (0.9 ms, pH 6.3). Diluted plasma was then circulated through the equilibrated cartridge assembly at 300 ml/min at 30 psi. The protein breakthrough was monitored using a Gilson UV monitor and the sample was collected in fractions for further analysis by electrophoresis. The cartridge assembly was eluted with 25 liters of 0.2M monophosphate buffer at pH 4.15, conductivity 9.5 ms in salt gradient form.

EXAMPLE 14

Identification of the Protein Components

The eluents were collected separately from each cartridge of Example 13 and the protein components characterized by the Helena Electrophoresis Densitomer. In the Helena procedure, the proteins are separated according to their respective electrical charges at pH 8.8 on cellulose acetate. Albumin, the smallest of the plasma protein molecules, with the largest number of negatively charged groups, has the fastest anodic migration. After the proteins were separated, the cellulose acetate plate was placed in a solution of sulfosalicylic and trichloroacetic acid to precipitate out the proteins. The proteins were fixed on the plate and Ponseau S applied to the proteins to stain the protein bands. Ponseau S at a pH less than 10 stains proteins in red color and has an adsorption peak at 525 nm. The staining intensity is linearly related to protein concentration. The first three liters of serum were over 99% pure, the purity reducing to less than 98% after 5 liters were collected. The major impurity was found to be transferrin.

One impurity of starting plasma yielded approximately 8.0 g of IgG. DEAE cellulose powder packed columns yield 5.3 g of IgG. Further, it is estimated that the Cohn process yields approximately 4.2–4.3 g/liter.

EXAMPLE 15

Separation of Plasma Components by QAE Cartridge

A synthetic protein mixture was prepared by mixing 300 mg HSA, 170 mg transferrin, and 250 mg of HGG. The protein mixture was dissolved in 13 ml 0.01M dibasic phosphate, the pH adjusted to 7.0 by using 0.01M monobasic sodium phosphate. A QAE cartridge prepared according to Example 2 was equilibrated to pH 7.0 with 0.01M phosphate solution. 22.6 ml of the protein solution was run into the equilibrated cartridge at 22 ml/min. The cartridge was washed with the starting buffer (0.01M phosphate, pH 7.0) until the $O.D._{280}$ dropped significantly. The eluted protein was later identified as HGG. A phosphate buffer (1.5 liters, 0.02M, pH 6.5) was run at 78 ml/min to bring the $O.D._{280}$ to a point approaching the base line. Transferrin was eluted with phosphate buffer (1.65 liters, 0.05M, pH 5.9). HSA was eluted with monobasic phosphate (1.00 liters, 0.1M, pH 4). The purity was checked by cellulose acetate electrophoresis in Helena Quick Scan Densitometer, the purity greater than 95%.

EXAMPLE 16

Fractionation of Prefiltered Human Plasma On 250 ml QAE Cartridge 50 ml of prefiltered human plasma, diluted to 250 ml with distilled water prior to filtration, was pH-adjusted to a pH of 7.8 and introduced into a 250 ml QAE media-containing cartridge (prepared as in Example 2), the cartridge having been equilibrated with sodium phosphate (0.01M, pH 7.8), at a flow rate of 15.4 ml/min. Two gamma globulin-containing fractions were obtained, Fractions A and B (see below), the fractions obtained following a 50 ml/min wash with equilibration buffer.

A continuous gradient was applied to the bound fraction (0.01M sodium phosphate buffer, pH 7.8, and 0.07M monosodium phosphate buffer, pH 4.7). Fraction C contained a mixture of betaglobulins (83%) and transferrin (17%). Fraction D contained 110 mg of transferrin, 85% pure. Fraction E contained 1.6 grams of albumin, better than 95% pure.

The purities of the fractions were checked by cellulose acetate electrophoresis and by Helena Quick Scan Densitometer using 520 nm filter. Table XX below characterizes the isolated plasma fractions.

TABLE XX

Characterization of Isolated Fractions of Plasma

| Fractions | Volume (liters) | pH | Conductivity (mS) | Purity (%) | Amount (gm) |
|---|---|---|---|---|---|
| Fr. A | 0.72 | 7.8 | 2.9 | 100 | 0.23 |
| Fr. B | 1.2 | 7.8 | 2.9 | 100 | 0.12 |
| Fr. C | 1.6 | 6.5 | 2.12 | | 0.07 |
| Fr. D | 1.9 | 5.9 | 2.90 | >95 | 0.11 |
| Fr. E | 7.6 | 5.2 | 3.7 | >95 | 1.6 |

Thus, it may be seen that the quaternized cellulose-GMA-DEAEMA matrix, in cartridge form, is fully capable of separating IgG from albumin and transferrin. At the same time, the albumin and transferrin may be recovered as by-product by eluting from the cartridge using a gradient elution.

EXAMPLE 17

Plasma Fractionation by Cellulose-GMA-DEAEMA Matrix (Example 1) In Cartridge Form

A. Materials

1. Plasma

The frozen plasma received from the local Red Cross was thawed and diluted with D.I. $H_2O$ at 10:1 ratio then adjusted to pH 6.3 by 0.5M HCl, the insoluble proteins precipitated out during the dilution removed by filtering through the filtration/adsorption cartridge of FIG. 3.

2. Ion Exchange Cartridge 8 of 3 high cartridges were connected in series. The total weight of matrix in the cartridge assembly was approximately 2,400 grams. The cartridges were swelled and equilibrated by passing 48 liters 0.1M phosphate buffer, pH 6.75 at 500 ml/min. followed with 0.01M phosphate buffer, pH 6.4 untill the conductivity and pH of the effluent are the same as those of the buffer (0.9 m.s. pH 6.3).

B. Preparation Procedure

1. Ion Exchange Chromatography a. Cartridge Operating Condition: 5 liters of human plasma, diluted 10:1 with D.I. $H_2O$, was applied to the equilibrated cartridge assembly at 300 ml/min. under 30 psi. The protein breakthrough was monitored using a Gilson U.V. monitor and the sample was collected in fractions to identify its purity by electrophoresis. The 8 cartridge unit was eluted with 25 liter 0.2M monophosphate buffer at pH 4.15 conductivity 9.5 m.s. in salt gradient form. The eluents were collected separately from each cartridge and the protein components were characterized by the Helena electrophoresis densitomer.

b. Identification of the Protein Components: In the Helena procedure, the proteins were separated according to their respective electrical charges at pH 8.8 on cellulose acetate. Albumin, the smallest of the plasma protein molecules with the largest number of the negatively-charged groups, had the fastest anodic migration. The gamma zone moved to the cathodic side. After the proteins were separated, the cellulose acetate plate was placed in a solution of sulfosalicyclic and trichloroacetic acid to precipitate out the proteins to be fixed on the plate. Ponceau S was applied to stain the protein bands. Ponceau S, at pH less than 10, stains proteins in red color and has an adsorption peak at 525 nanometer. The staining intensity is linearly related to protein concentration. The proteins eluted from the 8 cartridges were characterized by this procedure.

c. Total Material Balance and Estimation of Yield:

The total material balance is shown in Table XXI below. The filtrate contained 43.4 grams of IgG, the IgG having a purity of greater than 97%.

d. Recovery of Albumin and Transferrin in Plasma Fractionation:

The other two valuable components in plasma are albumin (40 g/l) and transferrin (2.95 g/l IEP=5.9). They were adsorbed in the cartridge at pH 6.3 and can be recovered separately under different salt concentrations as shown in the examples below. The transferrin and albumin, thus separated, were further purified by the cation exchanger cartridge of either SP (Example 3) or CM (Example 4) type. A recycle system according to FIG. 2 enabled the recovery of other components in plasma with high yield and minimum protein loss.

TABLE XXI

| Cartridge # | Vol. (liter) | Total Proteins | Major Protein Components |
|---|---|---|---|
| 1 | 14.0 | 68.6 g | & Globulin, Albumin |
| 2 | 7.5 | 19.5 | >95% Albumin |
| 3 | 14.0 | 58.8 | >95% Albumin |
| 4 | 10.0 | 12.0 | Globulin, Albumin |
| 5 | 2.5 | 5.5 | Transferrin, Albumin |
| 6 | 8.0 | 4.6 | Transferrin, Albumin |
| 7 | 8.0 | 3.9 | Transferrin, Albumin |
| 8 | 8.0 | 4.0 | >90% Transferrin |
| Total | 72.0 L | 176.9 g | |

EXAMPLE 18

Albumin Recovery From Human Plasma

As demonstrated in FIG. 2 and the text above referring thereto, in a preferred embodiment of the invention process for isolation and purification of IgG, recoveries are improved and various by-products are obtained by a recycle process wherein eluate from the initial ion-exchange chromatography is passed through a cartridge containing the SP stationary phase of Example 3 above.

Referring to FIG. 2, cartridge No. 1, a cellulose-GMA-DEAEMA stationary phase according to Example 1, is eluted with a 0.01M PB containing 30% sodium monophosphate, the eluate passed through a second cellulose-GMA-DEAEMA matrix-containing cartridge. The filtrate, containing transferrin, is passed into cartridge No. 3 and the transferrin recovered in accordance with the conditions set out in Example 19 below.

Each of cartridge Nos. 1 and 2 are eluted with 0.01M PB containing 100% sodium monophosphate, the eluate passing to cartridge No. 4, a sulfopropylated cellulose-GMA (Example 3) stationary phase contained therein. As shown in Table XXII below, substantial binding of human serum albumin (HSA) occurs at a pH as high as 5.6. But at pH 6.1, much less HSA binds; accordingly, cartridge No. 4 is equilibrated at pH 6.1. The filtrated contains the bulk of the HSA, with a small amount of the IgG retained on the stationary phase. This IgG is eluted back to cartridge No. 1 using acetate buffer at pH 8.0, containing 0.5 NaCl.

The CM matrix of Example 4 above is even more effective at recovering albumin.

TABLE XXII

| Binding Buffer pH | HSA Capacity per Cartridge (g) |
|---|---|
| 4.9 | 2.0 |
| 5.6 | 1.0 |
| 6.1 | 0.44 |
| 6.4 | 0.14 |

EXAMPLE 19

Transferrin Recovery

Referring again to FIG. 2, transferrin is originally captured on the cellulose-GMA-DEAEMA stationary phase of cartridge No. 1. Elution with 0.01M PB containing 30% monophosphate salt carries the transferrin through cartridge No. 2, also a cellulose-GMA-DEAEMA stationary phase into cartridge No. 3, a cellulose-GMA stationary phase which has been sulphopropylated with $Na_2SO_3$ (the carboxymethylated cellulose-GMA is also suitable). Any bound IgG can be eluted back to cartridge No. 1 using acetate buffer at pH 8.0 containing 0.5M NaCl. Transferrin at least 80% pure can be recovered from cartridge No. 4 by eluting with 0.05M sodium phosphate at pH 5.9.

We claim:

1. A method for production of high purity IgG from animal plasma, or a fraction thereof, comprising:
    (1) separating IgG from said animal plasma or fraction thereof to produce partially purified IgG by ion exchange chromatography using a chromatographic media comprising a matrix material comprising a first surface reactive group—containing substrate selected from the group consisting of silica, polysaccharide, or polypeptide, said surface reactive group being selected from the group consisting of the hydroxy group of silica, the hydroxy group of polysaccharide, or the amino group of polypeptide, said first substrate covalently bonded to a first synthetic polymer, said first synthetic polymer comprising:
        (a) a polymerizable compound containing an epoxy group capable of direct covalent coupling to said reactive group of said substrate; and
        (b) one or more polymerizable compounds containing:
            (i) an ionizable chemical group;
            (ii) a chemical group capable of transformation to an ionizable group;
    (2) separating high purity IgG from said partially purified IgG by affinity chromatography using a chromatographic media comprising a second matrix material comprising a second surface reactive group-containing substrate selected from the group consisting of silica, polysaccharide or polypeptide, said surface reactive group being selected from the group consisting of the hydroxy group of silica, the hydroxy group of polysaccharide, or the amino group of polypeptide, said second substrate covalently bonded to a second synthetic polymer, said second synthetic polymer comprising:
        (a) a polymerizable compound containing an epoxy group capable of direct covalent coupling to said reactive group of said second substrate; and
        (b) one or more polymerizable compounds containing a chemical group capable of causing the covalent coupling of said second synthetic polymer to an affinity ligand or a biologically active molecule.

2. The method of claim 1 wherein said animal plasma is bovine plasma.

3. The method of claim 1 wherein said animal plasma is human plasma.

4. The method of claim 1 and further including sterile filtration.

5. The method of claim 1 and further including sterile filtration followed by lyophilization.

6. The method of claim 1 wherein said ion-exchange matrix is in cartridge form.

7. The method of claim 6 wherein said first synthetic polymer comprises a homopolymer of a monomer capable of covalently bonding to said surface reactive groups of said first substrate and containing an ionic group or a group transformable to an ionic group.

8. The method of claim 7 wherein said homopolymer is selected from polyglycidyl acrylate or polyglycidyl methacrylate.

9. The method of claim 8 wherein said polyglycidyl acrylate or polyglycidyl methacrylate has been reacted with $Na_2SO_3$ or methacrylic acid.

10. The method of claim 6 wherein said first synthetic polymer comprises a copolymer of
    (a) a monomer capable of covalently bonding to said surface reactive groups and
    (b) a monomer containing an ionic group or a group transformable to an ionic group.

11. The method of claim 10 wherein said monomer (a) is selected from glycidyl acrylate and glycidyl methacrylate and said monomer (b) is selected from diethylaminoethyl methacrylate and diethylaminoethyl acrylate.

12. The method of claim 11 wherein said synthetic polymer is a copolymer of glycidyl methacrylate and diethylaminoethyl methacrylate.

13. The method of any one of claims 6–12 wherein said first substrate comprises a polysaccharide.

14. The method of claim 13 wherein said polysaccharide is cellulose.

15. The method of claim 1 wherein said second synthetic polymer comprises a homopolymer, said homopolymer being selected from the group consisting of polyglycidyl acrylate and polyglycidyl methacrylate.

16. The method of claim 15 wherein said homopolymer is polyglycidyl methacrylate.

17. The method of claim 16 wherein said second synthetic polymer is coupled to benzamidine, lysine or arginine.

18. The method of claim 17 wherein said second synthetic polymer is coupled to benzamidine.

19. The methods of any one of claims 15–18, wherein said second matrix material comprises a spirally wound swellable spaced apart matrix in sheet form.

20. The method of claim 19 wherein said second matrix is contained in a cylindrical housing with end caps having inlet and outlet orifices.

21. The method of claim 20 wherein said second substrate is a polysaccharide.

22. The method of claim 21 wherein said polysaccharide comprises cellulose.

23. A method for producing high purity IgG comprising:
(1) diluting animal plasma to decrease the plasma solubility of lipids, lipimic colloids, euglobulins and other non-IgG components;
(2) passing said diluted animal plasma through at least one separating column comprising a hollow cylinder and discs of solid stationary phase, said discs comprising at least one of activated carbon and at least one of fumed silica, to form a first filtrate containing IgG;
(3) chromatographically separating high purity IgG from said first filtrate, said chromatographic separation comprising:
(a) an ion-exchange chromatographic separation of said first filtrate to produce a second filtrate containing IgG free of proteins other than proteolytic enzymes;
said ion-exchange chromatographic separation effected with an ion-exchange matrix;
said ion-exchange matrix comprising a first surface reactive group-containing substrate selected from the group consisting of silica, polysaccharide or polypeptide, said surface reactive group being selected from the group consisting of the hydroxy group of silica, the hydroxy group of polysaccharide, or the amino group of polypeptide, said first substrate covalently bonded to a first synthetic polymer, said first synthetic polymer selected from a polymerizable compound containing an epoxy group capable of direct covalent coupling to said surface reactive group of said first substrate, said polymerizable compound selected from the group consisting of
  (i) homopolymers of a monomer capable of covalently bonding to said surface reactive groups of said first substrate and containing an ionic group or a group capable of transformation to an ionic group and,
  (ii) copolymers of a monomer capable of covalently bonding to said surface reactive groups of said first substrate and a monomer containing an ionic group or a group capable of being transformed into an ionic group;
(b) an affinity chromatographic separation of said second filtrate to produce a third filtrate comprising essentially pure IgG;
said affinity matrix comprising a second surface reactive group-containing substrate selected from the group consisting of silica, polysaccharide or polypeptide, said surface reactive group being selected from the group consisting of the hydroxy group of silica, the hydroxy group of polysaccharide, or the amino group of polypeptide, said second substrate covalently bonded to a second synthetic polymer, said second synthetic polymer selected from a polymerizable compound containing an epoxy group capable of direct covalent coupling to said surface reactive group of said second substrate, said polymerizable compound selected from the group consisting of
  (i) homopolymers of a monomer capable of covalently bonding to said surface reactive groups of said second substrate and containing a chemical group capable of coupling to an affinity ligand or a biologically active molecule;
  (ii) copolymers of a monomer capable of covalently bonding to said surface reactive groups of said second substrate and a monomer containing a chemical group capable of coupling to an affinity ligand or a biologically active molecule
said ion-exchange matrix comprising a swellable fibrous matrix in sheet form, spirally wound and spaced apart;
said ion-exchange matrix contained in a cylindrical housing with end caps having inlet and outlet orifices;
said affinity matrix comprising a swellable, spirally wound, spaced apart fibrous matrix in sheet form, contained in a cylindrical housing with end caps having inlet and outlet orifices.

24. The method of claim 23 wherein said diluted animal plasma in passed through two column filters, in series, the first of said two column filters containing discs of activated carbon, the second containing discs of fumed silica.

25. The method of claim 23 wherein said separating column comprises a single column containing activated carbon discs and fumed silica discs.

26. The method of claim 23 wherein said ion-exchange matrix comprises a cellulose substrate covalently bound to a synthetic polymer selected from (1) homopolymers of glycidyl acrylate or glycidyl methacrylate, in ionized form, (2) copolymers of glycidyl acrylate or glycidyl methacrylate and diethylaminoethyl acrylate or diethylaminoethyl methacrylate, and (3) quaternized copolymers of glycidyl acrylate or glycidyl methacrylate and diethylaminoethyl acrylate or diethylaminoethyl methacrylate.

27. The method of claim 23 wherein said affinity matrix comprises a cellulose substrate covalently bound to a synthetic polymer selected from polyglycidyl acrylate and polyglycidyl methacrylate, said polymer coupled to an affinity ligand.

28. The method of claim 27 wherein said affinity ligand is benzamidine.

29. The method of any of claims 26 or 27 wherein said synthetic polymer is crosslinked.

30. The method of claim 23 and further including a sterile filtration step.

31. The method of claim 30 and further including a lyophilization step.

32. A continuous method for obtaining intravenously injectable IgG, in high yield, highly pure transferrin, and highly pure albumin from animal plasma comprising:

(1) diluting said animal plasma to form diluted animal plasma;

(2) filtering or adsorbing said diluted animal plasma to separate sparingly soluble and precipitated plasma components, whereby a first filtrate is formed;

(3) passing said first filtrate through a first ion-exchange column, said first ion-exchange column containing an ion-exchange matrix materal comprising a first surface reactive group-containing substrate selected from the group consisting of silica, polysaccharide or polypeptide, said surface reactive group being selected from the group consisting of the hydroxy group of silica, the hydroxy group of polysaccharide, or the amino group of polypeptide, said substrate covalently bonded to a synthetic polymer, said synthetic polymer comprising:

(a) a polymerizable compound containing an epoxy group capable of direct covalent coupling to said reactive group of said substrate; and (b) one or more polymerizable compounds containing:

(i) an ionizable chemical group;

(ii) a chemical group capable of transformation to an ionizable group, to form a first adsorbed fraction retained on said first ion-exchange column and a first unadsorbed fraction which has passed through said first ion-exchange column, said first unadsorbed fraction containing a predominance of the IgG contained in said animal plasma, said first adsorbed fraction containing some IgG, essentially all the transferrin, and essentially all the albumin;

(4) eluting said first ion-exchange column to form a first eluate, said first eluate containing essentially all of the transferrin present in said animal plasma, and a portion of the albumin contained in said animal plasma;

(5) further eluting said first ion-exchange column to form a second eluate containing the residual of the albumin originally adsorbed on said first ion-exchange column;

(6) passing said first eluate from (4) through a second ion-exchange column, said second ion-exchange column containing a matrix material as in said first ion-exchange column, to form a second adsorbed fraction, said second adsorbed fraction containing essentially all of the albumin in said first eluate, and a second unadsorbed fraction, said second unadsorbed fraction containing essentially all of said transferrin in said first eluate;

(7) passing said second unadsorbed fraction from (6) through a third ion-exchange column, said third ion-exchange column containing a matrix as in said first ion-exchange column, said third ion-exchange column equilibrated at pH 5.8, thereby forming a third unadsorbed fraction and a third adsorbed fraction, said third unadsorbed fraction being essentially pure transferrin, said third adsorbed fraction containing residual IgG;

(8) eluting said second adsorbed fraction in said second ion-exchange column from (6) to form a third eluate containing the albumin from said second bound fraction;

(9) combining said second eluate from (5) and said third eluate from (8) to form a combined eluate and passing said combined eluate through a fourth ion-exchange column, said fourth ion-exchange column containing a matrix material as in said first ion-exchange column, thereby forming a fourth unadsorbed fraction and a fourth adsorbed fraction, said fourth unadsorbed fraction being high purity albumin, said fourth adsorbed fraction containing small amounts of residual IgG;

(10) recycling the residual IgG from (9) to said first ion-exchange cartridge by eluting said fourth adsorbed fraction;

(11) recycling the residual IgG from (7) back through said first ion-exchange column by eluting said third adsorbed fraction, where it joins fresh diluted, filtered animal serum and the process repeats itself;

(12) further purifying said first unadsorbed fraction from (3), whereby highly purified intravenously injectable IgG in high yield is obtained as a primary product and highly pure albumin and transferrin are obtained as by-product.

33. The method of claim 32 wherein said animal plasma is human plasma.

34. The method of any one of claims 32 or 33 wherein said further purifying said first unadsorbed fraction comprises:

(a) passing said first unbound fraction through an affinity chromatography column.

35. The method of claim 34 wherein said affinity chromatography column comprises a stationary phase which is cellulose-GMA with benzamidine ligand coupled thereto.

* * * * *